US008742186B2

(12) United States Patent
Gartside et al.

(10) Patent No.: US 8,742,186 B2
(45) Date of Patent: *Jun. 3, 2014

(54) BATCH PROCESS AND SYSTEM FOR THE PRODUCTION OF OLEFINS

(75) Inventors: Robert J. Gartside, Summit, NJ (US); Shaun M. McGovern, Hoboken, NJ (US); Thulasidas Chellppannair, Vestavia Hills, AL (US)

(73) Assignee: Lummus Technology Inc., Bloomfield, NJ (US)

( * ) Notice: Subject to any disclaimer, the term of this patent is extended or adjusted under 35 U.S.C. 154(b) by 685 days.

This patent is subject to a terminal disclaimer.

(21) Appl. No.: 12/936,284

(22) PCT Filed: Apr. 2, 2009

(86) PCT No.: PCT/US2009/002076
§ 371 (c)(1),
(2), (4) Date: Nov. 12, 2010

(87) PCT Pub. No.: WO2009/145834
PCT Pub. Date: Dec. 3, 2009

(65) Prior Publication Data
US 2011/0046425 A1    Feb. 24, 2011

Related U.S. Application Data

(60) Provisional application No. 61/072,993, filed on Apr. 4, 2008.

(51) Int. Cl.
*C07C 6/00* (2006.01)
*C07C 6/02* (2006.01)
*C07C 6/04* (2006.01)

(52) U.S. Cl.
USPC ............ 585/315; 585/643; 585/664; 585/670

(58) Field of Classification Search
CPC .............. C07C 2/00; C07C 6/02; C07C 6/04; C07C 6/00; C07C 5/25; C07C 5/2506; C07C 5/2556
USPC .................. 585/315, 316, 324, 643, 664, 670
See application file for complete search history.

(56) References Cited

U.S. PATENT DOCUMENTS 3,595,920 A    7/1971    Ellis et al.
4,615,769 A    10/1986    Horigome et al.
(Continued)

FOREIGN PATENT DOCUMENTS

EP    2259855 B1    12/2010
WO    03/076371 A1    9/2003

OTHER PUBLICATIONS

Ullmann, Fritz (2005). Ullmann's Chemical Engineering and Plant Design, vols. 1-2.. John Wiley & Sons. Online version available at: http://www.knovel.com/web/portal/browse/display?_EXT_KNOVEL_DISPLAY_bookid=3023&VerticalID=0.*

(Continued)

*Primary Examiner* — Walter D Griffin
*Assistant Examiner* — Jelitza Perez
(74) *Attorney, Agent, or Firm* — Osha • Liang LLP

(57) ABSTRACT

Described herein is a process for producing an alpha olefin by obtaining a feed stream of internal olefins having a first carbon number and alpha olefins having a first carbon number. The olefins are isomerized to increase the quantity of the alpha olefins. The olefins are then fractionated, subjecting the overhead material to catalytic metathesis to produce a mixed olefin effluent of internal olefins having a second carbon number and other hydrocarbons. The first isomerization reactor and fractionator are prepared to receive the olefins having a second carbon number, where the internal olefin intermediate is isomerized in the prepared first isomerization reactor. The second isomerization effluent is fractionated in the prepared first fractionator to separate the alpha olefins having the second carbon number from the internal olefins having the second carbon number. A corresponding system is also described, along with a heat pump that may be incorporated into the process.

23 Claims, 5 Drawing Sheets

(56) References Cited

U.S. PATENT DOCUMENTS

| | | | |
|---|---|---|---|
| 4,709,115 A | 11/1987 | Jung et al. | |
| 5,057,638 A | 10/1991 | Sweeney | |
| 5,386,075 A | 1/1995 | Keil et al. | |
| 6,589,395 B1 | 7/2003 | Meili | |
| 6,727,396 B2* | 4/2004 | Gartside | 585/324 |
| 6,777,582 B2 | 8/2004 | Gartside et al. | |
| 6,875,901 B2 | 4/2005 | Gartside et al. | |
| 7,132,038 B2 | 11/2006 | Bohner et al. | |
| 2002/0183572 A1 | 12/2002 | Gartside | |
| 2005/0124839 A1* | 6/2005 | Gartside et al. | 585/643 |
| 2006/0235253 A1 | 10/2006 | Gartside et al. | |
| 2008/0119676 A1* | 5/2008 | Hildreth et al. | 585/314 |

OTHER PUBLICATIONS

Tomazi et al. Batch Processing Industries. Batch Processes. Chapter 2, 2005, pp. 7-10 and 27-28. http://books.google.com/books?id=zlzwOEtDu4lC&printsec=frontcover&source=gbs_atb#v=onepage&q&f=false.*

Griesbaum et al. Hydrocarbons. Ullmann's Encyclopedia of Industrial Chemistry, 2000, p. 157. http://onlinelibrary.wiley.com/doi/10.1002/14356007.a13_227/full#a13_227-sec1-0002.*

Correspondence reporting Office Action dated Dec. 18, 2012 in corresponding Japanese Patent application 2011-502987 (4 pages).

Examination Report issued Jul. 6, 2012 in corresponding Mexican application No. MX/a/2010/010836 (2 pages).

Invitation to Respond to Written Opinion mailed Aug. 24, 2011 in corresponding Singapore Patent Application No. 201007126-4 (11 pages).

International Search Report from PCT/US2009/002076 dated Nov. 2, 2009 (2 pages).

Written Opinion from PCT/US2009/002076 dated Nov. 2, 2009 (6 pages).

First Office Action dated Dec. 5, 2012 in corresponding Chinese application No. 200980111417.2 (5 pages).

Notice of Decision to Refuse a Patent (wltranslation) issued Mar. 28, 2013 in corresponding Korean application No. 10-2010-7024865 (5 pages).

Substantive Examination Report (w/translation) issued in corresponding Indonesian application No. W-00201003216 (2 pages).

Office Action issued Aug. 31, 2012 (w/translation) in corresponding Korean application No. 10-2010-7024865 (9 pages).

* cited by examiner

BATCH PROCESS AND SYSTEM FOR THE PRODUCTION OF OLEFINS

RELATED APPLICATIONS

This application claims priority from U.S. Provisional Application 61/072,993 filed Apr. 4, 2008.

BACKGROUND

The disclosed embodiments generally relate to processes and systems for producing alpha olefins and more particularly to a batch process for the production of alpha olefins.

A conventional process for production of comonomer grade hexene-1 from $C_4$ raffinate feed streams is a continuous process that has three stages. First butene-1 is separated from the feed stream in a $C_4$ fractionator. The butene-2 in the fractionator bottoms stream is isomerized to butene-1 and recycled to the fractionator. Second, the butene-1 is sent to an autometathesis reactor to form ethylene and hexene-3. The reactor effluent is sent to a depentanizer to separate hexenes. The products are lights that go overhead, the hexene-3 is a liquid bottoms product, and the $C_4/C_5$ products are recycled. Third, the hexene-3 feed is isomerized and the hexene-1 product is separated in a $C_6$ fractionator.

U.S. Pat. No. 6,727,396 (Gartside, April 2004) describes a continuous process for production of hexene-1, combining the isomerization and metathesis steps. Typical metathesis reactions are described in U.S. Pat. No. 3,595,920 (Ellis et al, July 1971). U.S. Pat. No. 4,709,115 (Jung et al, November, 1987) discusses improving the selectivity and conversion of butene-1 and butene-2 to hexene-3 by using catalytic distillation. The removal of the lighter components pushes the reaction equilibrium toward the heavy products. U.S. Pat. No. 5,057,638 (Sweeney, October 1991) discusses a method for production of hexene-1 from butene-1 in which the butene-1 is metathesized to hexene-3. Subsequently, a hydration/dehydration procedure is applied to produce a mixture of n-hexenes containing hexene-1.

Various other processes are known for the processing of $C_4$ olefins. U.S. Pat. No. 6,875,901 (Gartside et al, April 2005) describes olefin isomerization technology used for production of terminal olefins. The process is applied to the production of butene-1 from butene-2. U.S. Pat. No. 6,777,582 (Gartside et al, August 2004), describes butene-1 autometathesis technology, including differences from the conventional metathesis reaction of butene-2 and ethylene to produce propylene.

Closed-loop heat pumps are used in various processes. U.S. Pat. No. 6,589,395 describes a process in which a closed-loop heat pump is included on a general distillation tower. This document describes the use of a heat source and heat sink that can be substituted for the heat pump should the compressor fail. U.S. Pat. No. 5,386,075 (Keil et al, January 1995) and U.S. Pat. No. 4,615,769 (Horigome et al, October 1986) discuss the use of an open-loop heat pump in an ethylbenzene/styrene distillation.

It would be useful to develop a process for producing alpha olefins that has improved efficiency when operated on a small scale.

SUMMARY

One embodiment is a process for producing an alpha olefin comprising obtaining a feed stream comprising an internal olefin having a first carbon number and an alpha olefin having a first carbon number, isomerizing the feed stream in a first isomerization reactor to increase the quantity of the alpha olefin having the first carbon number, forming a first isomerization effluent, fractionating the first isomerization effluent in a first fractionator to obtain a bottoms stream comprising the internal olefin having the first carbon number and an overhead stream comprising the alpha olefin having the first carbon number, subjecting the overhead stream to catalytic metathesis in a metathesis reactor under conditions and in the presence of a first metathesis catalyst to produce a mixed olefin effluent comprising an internal olefin having a second carbon number and other hydrocarbons, fractionating the mixed olefin effluent in a second fractionator to remove at least a portion of the other hydrocarbons and obtain an internal olefin intermediate, preparing the first isomerization reactor to receive the internal olefin intermediate, isomerizing the internal olefin intermediate in the prepared first isomerization reactor to form a second isomerization effluent comprising an increased quantity of alpha olefins having the second carbon number, preparing the first fractionator to receive the second isomerization effluent, and fractionating the second isomerization effluent in the prepared first fractionator to separate the alpha olefin having the second carbon number from the internal olefin having the second carbon number. In some embodiments, a portion of the butene-1 is removed from the first fractionator as butene-1 product.

Another embodiment is a process for producing hexene-1 comprising obtaining a $C_4$ feed containing butene-1 and butene-2, isomerizing butene-2 to butene-1 in a first isomerization reactor, forming a first isomerization reactor effluent, fractionating the first isomerization reactor effluent in a first fractionator to form an overhead stream comprising butene-1 and a bottoms stream comprising butene-2, subjecting at least a portion of the overhead product to catalytic metathesis in a first metathesis reactor under conditions and in the presence of a first metathesis catalyst to produce a mixed olefin effluent comprising ethylene and hexene-3, fractionating the mixed olefin effluent in a second fractionator to form a hexene stream comprising hexene-3 and an overhead product stream comprising ethylene, preparing the first isomerization reactor to receive the hexene stream, isomerizing the hexene stream to form a second isomerization effluent comprising hexene-1 and hexene-2 and the remaining hexene-3, preparing the first fractionator to receive the second isomerization effluent, and fractionating the second isomerization effluent in the prepared fractionator to obtain a hexene-1 stream.

Yet another embodiment is a system for producing an alpha olefin, comprising a first isomerization reactor configured to isomerize a first batch of an olefin having a first carbon number to form a first isomerization reactor effluent and subsequently process a second batch of an olefin having a second carbon number to form a second isomerization reactor effluent, a metathesis reactor positioned downstream from the first isomerization reactor, the metathesis reactor being configured to disproportionate the first isomerization reactor effluent to form a metathesis reaction product, a first fractionator positioned downstream from the isomerization reactor and being configured to separately fractionate the first and second isomerization reactor effluents, a second fractionator positioned downstream from the metathesis reactor to remove light hydrocarbons from the metathesis reaction product, a storage tank disposed downstream from the first or second fractionator, and a storage tank outlet line connecting the storage tank to an inlet of the first isomerization reactor and/or to the inlet of the metathesis reactor.

DETAILED DESCRIPTION

The embodiments described herein employ a process operated in a campaign or sequential processing mode with a single isomerization reactor, a single superfractionator following the isomerization, and one or more metathesis reactors with subsequent fractionation to obtain intermediate olefins streams, and to obtain a desired olefin product or products. The separation of closely boiling double bond isomers of any single carbon number requires significant energy and equipment. By using a single superfractionator (or set of 2 superfractionators) to separate isomers having a first carbon number in a first separation process and to then subsequently use the same superfractionator (or set of superfractionators) to separate isomers having a second carbon number in a second separation process, certain efficiencies can be realized. Similarly, by using a single isomerization reactor to isomerize a compound having a first carbon number in a first isomerization process and a compound having a second carbon number in a second isomerization process, processing advantages will be achieved. The process can be used with feed streams having carbon chains with a variety of carbon numbers to produce product streams having desired carbon numbers. The process is particularly useful for producing alpha olefins.

Figure 1:
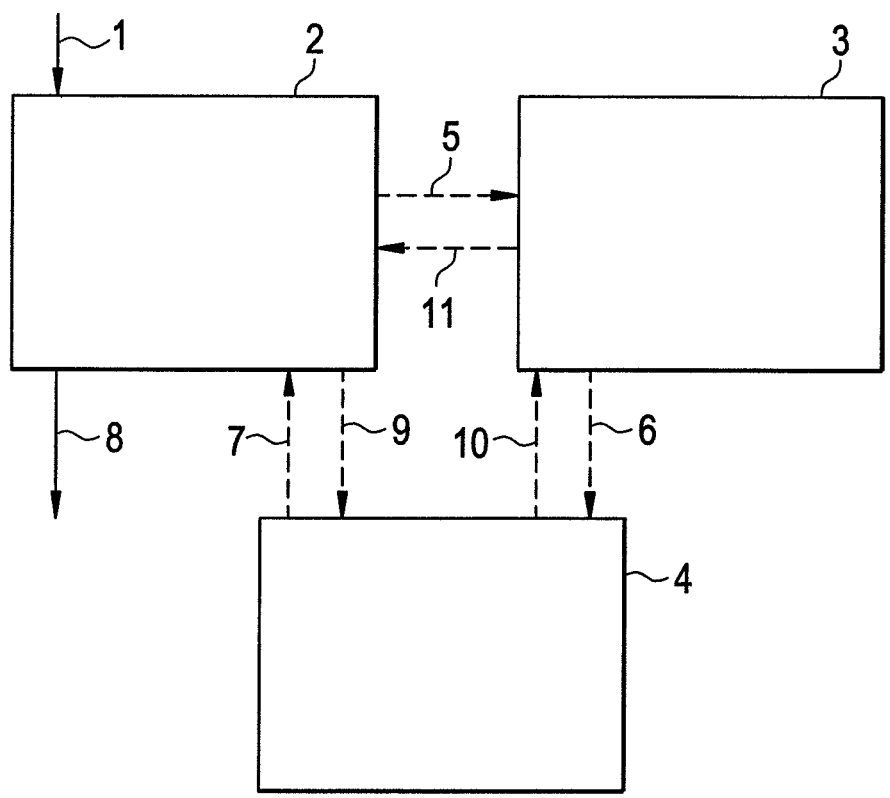
FIG. 1 is a schematic drawing showing three sections of the system described herein.

FIG. 1 illustrates a system that includes an isomerization and fractionation section 2, a metathesis and fractionation section 3 and a storage section 4. While the descriptions of FIGS. 1-8 refers to C4 and C6 hydrocarbons, hydrocarbons with other carbon numbers also can be processed in the systems that are described. A fractionator/isomerization reactor combination, designated as 2 and termed the "superfractionator system", first operates in $C_4$ service. Mixed $C_4$'s are introduced at 1 and are isomerized and then fractionated at 2 to form a butene-1 isomerization product. The butene-1 isomerization product is fed continuously at 5 to the metathesis and fractionation section 3 in which metathesis takes place. The metathesis reactor effluent is fractionated to form light products including ethylene and a hexene-3 product which is fed at 6 to a storage tank at 4. When sufficient hexene-3 has accumulated in the storage tank, the isomerization and fractionation section 2 is prepared for alternate service. The hexene-3 from the tank is then sent at 7 to the isomerization and fractionation section 2 system now in $C_6$ service, where the hexene-3 is isomerized and fractionated to form the hexene-1 product, which is removed at 8.

In another configuration, the mixed $C_4$'s are processed in the isomerization and fractionation system 2 to form butene-1. The butene-1 stream is sent at 9 to the storage section 4. When sufficient butene-1 has accumulated, the isomerization and fractionation system 2 is prepared for alternate service. A portion of the butene-1 optionally can be removed as a product and the remaining portion is fed at 10 to the metathesis and fractionation section 3. The metathesis reactor effluent is fractionated to produce light products including ethylene and a hexene-3 stream. The hexene-3 stream is then sent at 11 to the isomerization and fractionation section 2 where the hexene-3 is isomerized and the mixed hexene stream fractionated to form hexene-1 product, which is removed at 8.

In all embodiments, all or part of the internal olefin stream from the bottom of the superfractionator separation may be recycled to the isomerization reactor to produce more butene-1 or hexene-1.

In a larger scale conventional, continuous autometathesis process, separate $C_4$ and $C_6$ systems are employed, allowing heat integration between the systems to reduce utilities. For the campaign operation systems described herein, an alternate means of reducing utility costs is used to achieve savings. More specifically, in certain embodiments, a heat pump is included in a campaign system designed to produce olefins such as polymer-grade hexene-1. The heat pump provides a heat-integrated fractionator, whereby the tower's condenser and reboiler share a common heat transfer fluid. An open-loop heat pump uses the tower overhead stream as the heat transfer fluid. A closed-loop heat pump uses an alternate fluid. The alternate fluid is chosen based upon the specific thermodynamic properties to allow for condensing and reboiling duties to be achieved within reasonable pressures such that compression duties are minimized. For systems operating in campaign mode, the choice of alternate fluid is especially advantageous since it must operate to achieve condensing and reboiling duties in the fractionation of two different carbon numbers.

Figure 2:
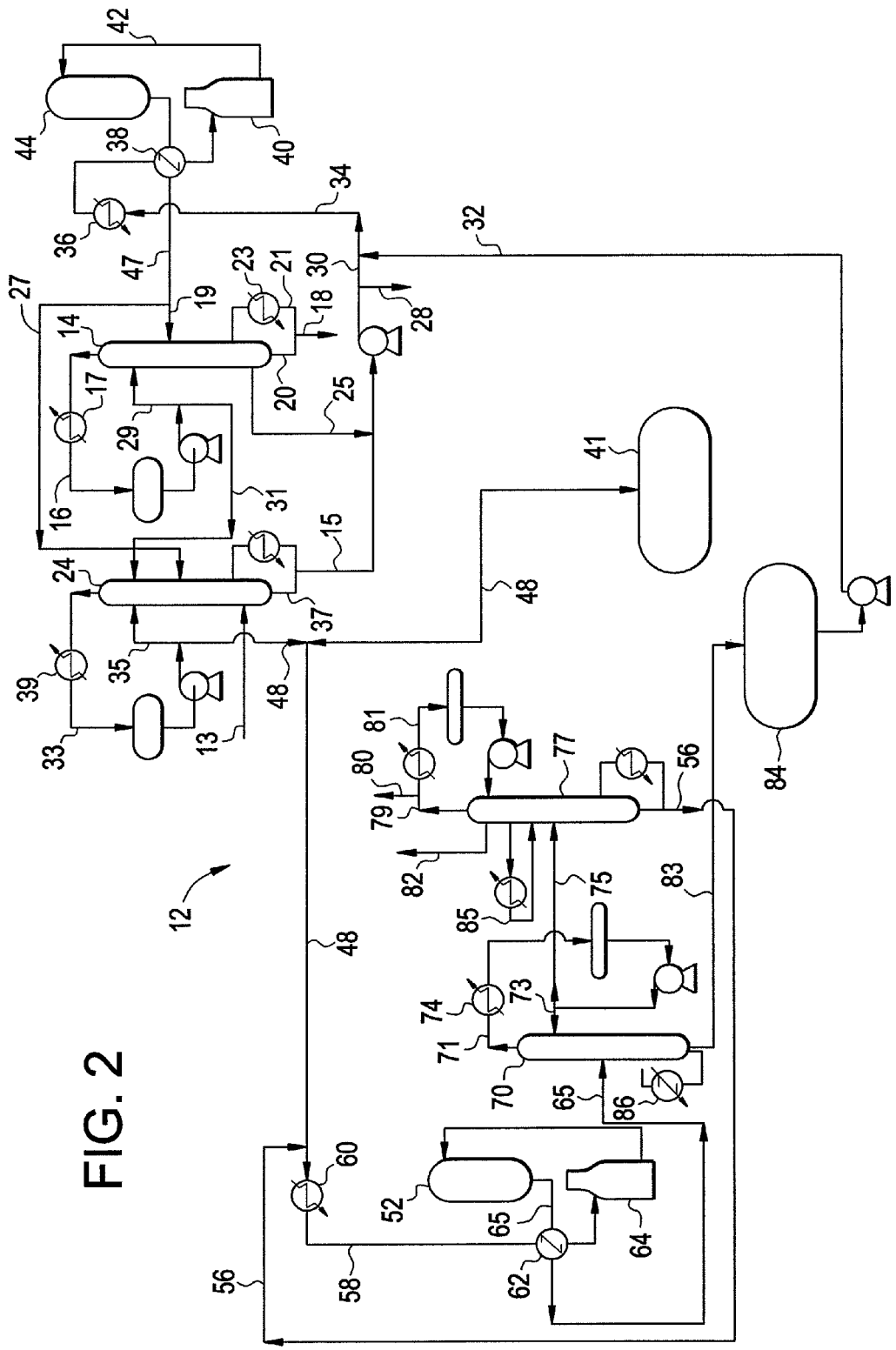
FIG. 2 is a process flow diagram showing a first embodiment.

Referring to FIG. 2, a process flow diagram for a campaign process for sequentially producing butene-1 and hexene-1 is shown. The overall process is designated as 12. One portion of the equipment is used in $C_4$ service only, a second portion of equipment is used in $C_6$ service only, and a third set of equipment is shared between both services.

The butene separation system consists of two towers operated with different pressures to allow for energy interchange between them to reduce overall utilities. Tower 14 is considered tower 1 and tower 24 is considered tower 2. Tower 1 operates at a higher pressure than tower 2. This allows the temperature of tower 1 overhead condenser 17 to be at a higher temperature than tower 2 reboiler. Since heat is removed in the condenser 17 and supplied to a reboiler 86, these can be exchanged without separate external heat being required. The key to this system is to balance the duties to allow them to be matched. This matching is conventionally done by bypassing a side draw from one tower to the other. Optimally however this is done by splitting the main feed to the tower with the proportion to each tower adjusted such that the exchanger duties can be matched. The main feed from the isomerization section 47 is split into line 19 to tower 1 and 27 to tower 2.

A $C_4$ raffinate in feed line 13, which contains butene-1 and butene-2, and usually also contains other $C_4$ hydrocarbons, enters the lower end of fractionator 24 in which butene-1 and butene-2 are separated. The bottoms line 15 from fractionator 24, which primarily contains butene-2, combines with line 25 (line 32 is not used in the $C_4$ processing phase) to form line 34, which enters the isomerization reactor loop, described below. The effluent of this loop in line 47 is split into line 19, which enters the middle of a fractionator 14, and line 27, which enters the middle of fractionator 24. In fractionator 14 an overhead product of butene-1 is taken in overhead line 16. The material in line 16 is condensed in a condenser 17, separated into a reflux line 29 for the fractionator 14 and a feed line 31 for the fractionator 13, in which further separation of butene-1 and butene-2 takes place.

Fractionator bottoms line 25 is removed from the bottom of the fractionator 14 and combined with line 15 as indicated above. A fractionator reboiler line 20 removes material at the bottom of the fractionator 14. A purge line 18 is taken off the fractionator reboiler line 20 to prevent buildup of any heavy hydrocarbons in the tower bottoms. The remainder of the fractionator bottoms in line 21 are reboiled in reboiler 23 and returned to fractionator 14 where they undergo separation.

Feed line 31 enters the fractionator 24 above the point of entry of feed line 27. Butene-1 is removed from the top of fractionator 24 in line 33 and butene-2 is removed from the bottom of fractionator 24 in line 37. The top line 33 is condensed in a condenser 39 and is divided into a reflux line 35 and line 48.

In the isomerization loop, the material in isomerization line 34 is vaporized in heat exchanger 36 and heated in heat exchanger 38 and then fed to a furnace 40. Vaporized line 42 from the furnace 40 is fed to an isomerization reactor 44 in which some of the butene-2 is isomerized to form butene-1. The $C_4$ effluent from the reactor 44 leaves at butene-1/butene-2 equilibrium. The reactor temperature defines the equilibrium and thus controls the composition. The reactor effluent line 47 is cooled in heat exchanger 38 and sent to the fractionator 14. It is apparent to one skilled in the art that if the $C_4$ feed line 13 contains butene-1 above the equilibrium level set by the isomerization reactor conditions, the feed line would be first sent to the tower 14 and the butene-1 content recovered overhead with the butene-2 being fed to the isomerization reactor 44. Alternately if the composition of C4 feed line 13 had little or no 1 butene, it could first be fed directly to the isomerization system.

Downstream from fractionator 24, the contents of line 48 are either sent to tank 41, or to another storage tank, where they are collected until ready for metathesis, or they are sent directly to the metathesis section for further processing, in which case tank 41 is not required. In FIG. 2, line 48 is shown as providing for flow both into and out of the storage tank 41. When metathesis is to take place, line 48 is combined with a recycle line 56 containing $C_4/C_5$ to form an autometathesis feed line 58, which is fed to an autometathesis reactor 52. Before metathesis, line 58 is vaporized in a heat exchanger 60, further heated in a heat exchanger 62, and then heated to reaction temperature in an autometathesis furnace 64. The contents of line 58 are then fed to the autometathesis reactor 52. Autometathesis is an equilibrium reaction in which hexene-3 is produced. Small amounts of side products propylene, pentene-2,2-methyl-pentene-2, and some C7s also are produced. In addition, a small amount of reverse isomerization of butene-1 to butene-2 occurs. Of these side products only 2-methyl-pentene-2, formed from the reaction of butene-1 with isobutylene, unfavorably affects the hexene-1 product purity because it boils lower than hexene-1 and is thus carried out with the overhead product of the final $C_6$ separation. Thus, the isobutylene content in the $C_4$ raffinate feed is required to be minimized to a level consistent with the desired hexene-1 specification.

The autometathesis effluent in line 65 is a mixture of $C_2$s through $C_7$s. The contents of line 65 are cooled in heat exchanger 62 to form a depentenizer feed line, which is sent to a fractionator 70 (operating here as a depentenizer). A $C_2/C_3$ overhead line 71 is removed from the fractionator 70. The overhead line 71 is condensed in a condenser 74 and divided into a reflux line 73 and a feed line 75 for a fractionator 77, which is operated here as a depropylenizer. The bottoms line 83 of fractionator 70 is sent to a $C_6$ storage tank 84 where it is held until the fractionation and isomerization equipment is ready for $C_6$ processing, or, if the equipment is ready, the bottoms line 83 proceeds directly to the fractionation and isomerization section as line 32 and tank 84 is not required. It is noted that one of the fractionators 24 and 14 can be run as the depentenizer 70 if the $C_4$ is stored at an appropriate time to allow for reconfiguration of the fractionator. Alternately fractionator 70 can be configured through piping to add additional fractionation stages to fractionators 14 and 24 thus providing additional flexibility for processing and capital and energy savings by allowing fractionators 14 and 24 to be slightly smaller.

The top line 79 from the fractionator 77 is divided into a C2/C3 line 80, which is sent to a steam cracker separation system, for example, and a reflux line 81. Line 82 is a side draw product line that is optionally installed to allow for recovery of a higher purity 1 butene stream from the unreacted 1 butene. A side draw 85 is removed and passed through a cooler to partially condense the vapor stream in the tower at that point when it is reintroduced. By cooling at a temperature consistent with cooling water at this point, the refrigeration commonly used in the overhead condenser can be reduced. The bottoms line 56 from the fractionator 77 contains $C_4$ and $C_5$ compounds and is combined with line 48 to form the metathesis feed stream.

Either before metathesis (but after $C_4$ isomerization and fractionation) or after production of a sufficient amount of hexene-3, the isomerization reactor 44 and fractionators 24 and 14 are prepared for $C_6$ service. The autometathesis reactor is not used in the second campaign if it was used in the first step to produce 3-hexene. The hexene-3 is fed from storage tank 84 in line 32. Line 32 becomes isomerization feed line 34. Line 34 is vaporized in heat exchanger 36, heated in heat exchanger 38, further heated in furnace 40, and fed as line 42 first to the isomerization reactor 44. The reactor effluent in line 47 is sent to the fractionators 24 and 14. The isomerization reactor 44, fractionator 24 and fractionator 14 are now operating in $C_6$ service.

In $C_6$ service, the fractionator 14 bottoms line 20 of $C_7^+$ is partially purged from the system in line 18, and the remainder is reboiled in reboiler 23 and returned to the fractionator as line 21. A side draw 25 of hexene-2 and hexene-3 is taken from a lower stage of the fractionator 14 (with the top defined as stage 1), combined with bottoms line 15 from fractionator 24, partially purged in line 28, and partially recycled to the isomerization reactor 44 in line 30. Line 30 combines with fresh hexene-3 feed 32 from the $C_6$ storage tank 84 to form isomerization reactor feed 34 (now operating in $C_6$ service). The overhead line 16 from fractionator 14 is divided into a reflux line 29 and a feed line 31 for the fractionator 24.

In the fractionator 24, hexene-1 is taken as overhead product in line 33. Line 33 is divided into reflux line 35 and line 48. Line 48 contains the hexene-1 product and is sent to tank 41. It is noted that the metathesis reactor is not involved in the processing of the $C_6$ line.

As indicated above, the shared equipment from the batch process flowsheet is designed for operation in both $C_4$ and $C_6$ service. Depending on the type of equipment, this can be handled in different ways. Heat exchangers, for example, may have varying temperature approaches, but the heat exchanger surface area may be adjusted by using multiple shells. Reactor capacity can be addressed by using multiple reactors. Because the fractionator towers cannot be handled in the same way as the heat exchangers or reactors, their design is chosen to remain fixed between services.

In order to use the same tower or towers as both the $C_4$ and $C_6$ fractionator, and if the second tower is used as both the depentanizer and as part of a $C_6$ fractionator, the tower sizing must be identical for the chosen flow rates. Because campaign operation allows for independent variation of the flow rates between $C_4$ and $C_6$ service, operating time can be used as a variable to adjust the flow rates such that a net yearly production of, e.g., 5 KTA hexene-1 is achieved. Using this approach, in one embodiment the $C_4$ process is operated for 2,000 hours and then the $C_6$ process is operated for 5,333 hours.

Overall, the shared use of the fractionator and isomerization system components in the batch process eliminates 35 of the 64 pieces of equipment from the continuous hexene-1 process. The continuous process has 2 complete superfractionator/isomerization reactor systems compared to just one for the campaign operation. The estimated reduction in total installed capital cost is about 35-45%. This makes campaign operation especially suited for smaller capacity installations. An example of a process using the configuration of FIG. 1 is provided below as Example 1.

Figure 3:
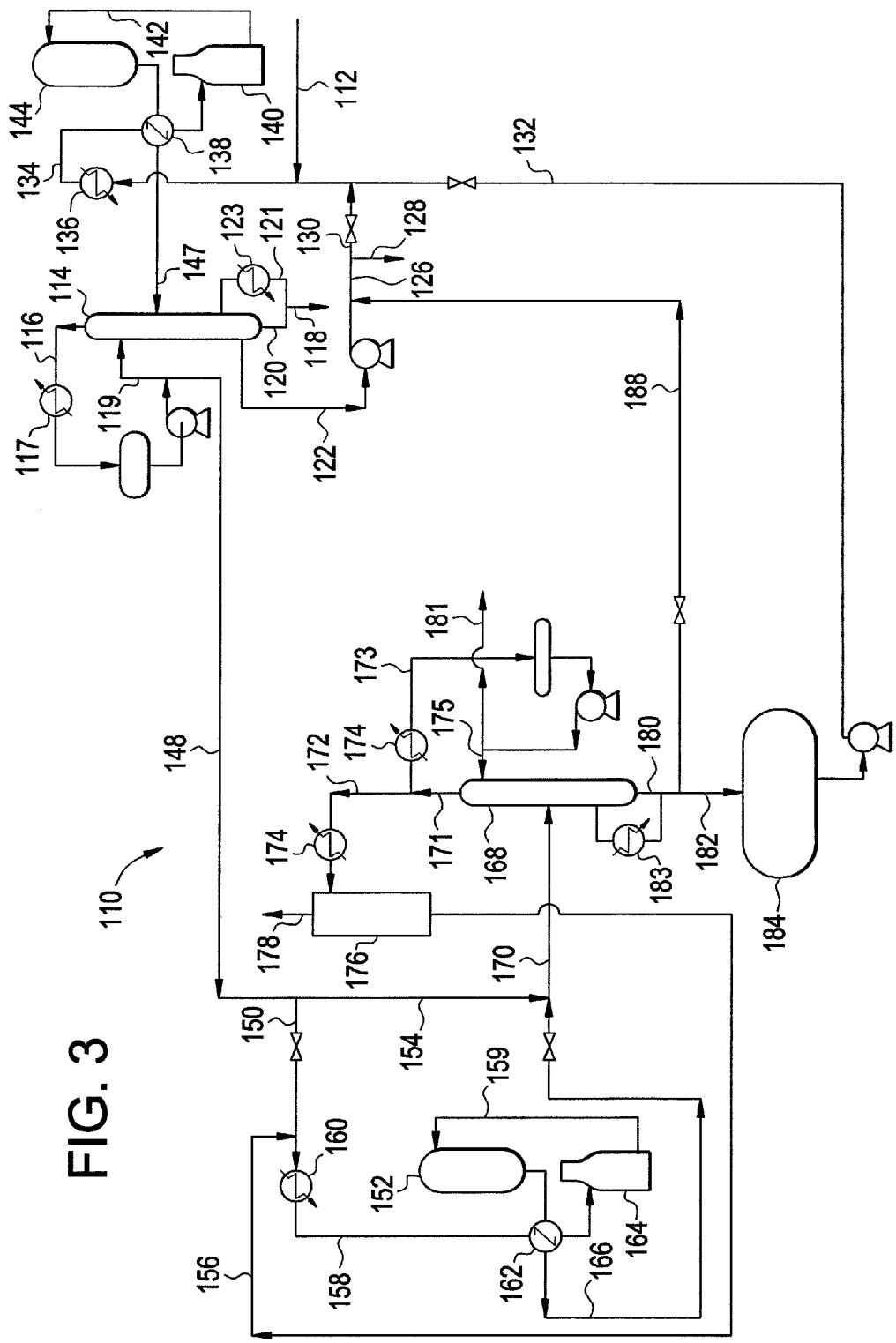
FIG. 3 is a process flow diagram showing a second embodiment.

Referring to FIG. 3, a process flow diagram for another campaign process for sequentially producing butene-1 and hexene-1 is shown. The overall process is designated as 110. One portion of the equipment is used in $C_4$ service only, a second portion of equipment is used in $C_6$ service only, and a third set of equipment is shared between both services.

A $C_4$ raffinate in feed line 112, which contains butene-1 and butene-2, and usually also contains other $C_4$ hydrocarbons, combines with the contents of line 134 and enters the isomerization reactor loop. The effluent of this loop in line 147 enters the middle of a fractionator 114. In fractionator 114 an overhead product of butene-1 is taken in overhead line 116. The contents of line 116 are condensed in a condenser 117.

Fractionator bottoms in line 122 are removed from the bottom of the fractionator 114, partially purged in a purge line 128, and the remaining material in line 130 is combined with the contents of $C_4$ feed line 112 (line 132 is not in use during the $C_4$ phase) to form isomerization feed line 134. Purge line 128 is provided to remove any n-butanes in the $C_4$ feed 112 that would accumulate in the system. A fractionator reboiler line 120 removes material at the bottom of the fractionator 114. A purge line 118 is taken off the fractionator reboiler line 120 to prevent buildup of any heavy hydrocarbons in the tower bottoms. The remainder of the fractionator bottoms in line 121 is reboiled in reboiler 123 and returned to fractionator 114 where it undergoes separation.

The contents of isomerization line 134 are vaporized in heat exchanger 136 and heated in heat exchanger 138 and then fed to a furnace 140. Vaporized material in line 142 from the furnace 140 is fed to an isomerization reactor 144, which in one embodiment is an equilibrium reactor operating at 343 C and 2978 kPa. The $C_4$ effluent from the reactor in this embodiment leaves at butene-1/butene-2 equilibrium with an approximate butene-1 concentration of 21%. The reactor effluent in line 147 is cooled in heat exchanger 138 and sent to the fractionator 114. The ratio of recycle to fresh feed in the fractionator is typically 2.4 to 1. It is apparent to those skilled in the art that if the $C_4$ feed in line 112 contains butene-1 above the equilibrium level set by the isomerization reactor conditions, the feed stream would be first sent to the tower 114 and the butene-1 content recovered overhead with the butene-2 being fed to the isomerization reactor 144.

The butene-1 product from the fractionator 114 in overhead line 116 is divided into a reflux stream in line 119 and intermediate product in line 148. The material in line 148 is sent into line 150 (line 154 is used for $C_6$ processing). The butene-1 in line 150 is combined with a recycle line 156 containing $C_4$/$C_5$ to form an autometathesis feed line 158, which is fed to an autometathesis reactor 152. The material in line 158 is vaporized in a heat exchanger 160, further heated in a heat exchanger 162, and then heated to reaction temperature in an autometathesis furnace 164. Vaporized material in line 159 is then fed to the autometathesis reactor 152. Autometathesis is an equilibrium reaction The autometathesis effluent in line 166 is a mixture of $C_2$s through $C_7$s. The material in line 166 is cooled in heat exchanger 162 to form a (depentenizer) feed line. The contents of line 170 are sent to a fractionator 168 (operating here as a depentenizer), which in one embodiment operates at 1200 kPa with 30 theoretical stages and a reflux ratio of 1.0. The temperature in the fractionator 168 typically is in the range of 60-100° C. A $C_2$/$C_3$ overhead line 171 is removed from the fractionator 168. Overhead line 171 is split into line 172 and line 173. The contents of overhead line 172 are cooled in heat exchanger 174 and sent to a flash drum 176. The light fraction from the flash drum comprising ethylene and propylene are purged in line 178 and can be recycled to the ethylene/propylene recovery section of an ethylene cracker. The $C_4$s-$C_5$s from the bottoms of the flash drum in line 156 still contain a significant amount of butene-1 and are recycled in line 156, which is combined with line 150 to form line 158, the feed line for the autometathesis reactor. The material in overhead line 173, when operating in $C_4$ mode, is condensed in a condenser 174 to form reflux for tower 168.

The fractionator bottoms line 180, separated to 98 mol % hexene-3, is divided into a hexene-3 line 182, a reboiler line 183, and a $C_6$ recycle line 188. In $C_4$ operating mode, the hexene-3 in line 182 fills a $C_6$ storage tank 184 and is used as the feed for the second phase of the campaign operation.

After production of a sufficient amount of hexene-3, the system is shut down and prepared for operation in $C_6$ service. The isomerization reactor 144, tower 114 and tower 168 are prepared for $C_6$ service. The autometathesis reactor is not used in the second campaign. The hexene-3 is fed from storage tank 184 in line 132. Line 132 becomes isomerization feed line 134. Material in line 134 is vaporized in heat exchanger 136 and heated in heat exchanger 138, then further heated in furnace 140, and fed as line 142 first to the isomerization reactor 144. In the isomerization reactor 144, approximately 8.9% conversion to hexene-1 occurs. The reactor effluent in line 147 is sent to the fractionator 114. Both the isomerization reactor 144 and fractionator 114 are now operating in $C_6$ service.

To make the campaign system work, the fractionation and isomerization equipment must be identical for $C_4$ and $C_6$ processing. The separation of the hexene-1 from the mixed hexene stream requires more fractionation than the separation of butene-1 from the butene-1/butene-2 stream in $C_4$ operation. One option is to design a tower oversized for $C_4$ operation but that will be appropriate for $C_6$ service. Another option is to use tower 168 to provide the additional fractionation capacity for $C_6$ operation since the autometathesis reactor is not used in $C_6$ operation. In this embodiment, tower 168 is used as the top portion of the $C_6$ fractionation receiving the overhead from tower 114.

The fractionator 114 bottoms stream of $C_7^+$ in line 118 is purged from the system. A side draw 122 of hexene-2 and hexene-3 is taken from a low stage of the fractionator 114 (with the top defined as stage 1) and recycled to the isomerization reactor 144 via lines 126 and 130. It is mixed with fresh hexene-3 feed 132 from the $C_6$ storage tank 184 to form isomerization reactor feed 134' (now operating in $C_6$ service). Purge line 128 is not in service. The overhead line 116 is separated to a desired ratio of hexene-1 and most of it is sent in line 148 to line 154 and then line 170 to fractionator 168 (formerly functioning as a depentenizer for $C_4$ service). It is noted that the metathesis reactor is not involved in the processing of the $C_6$ line.

Figure 5:
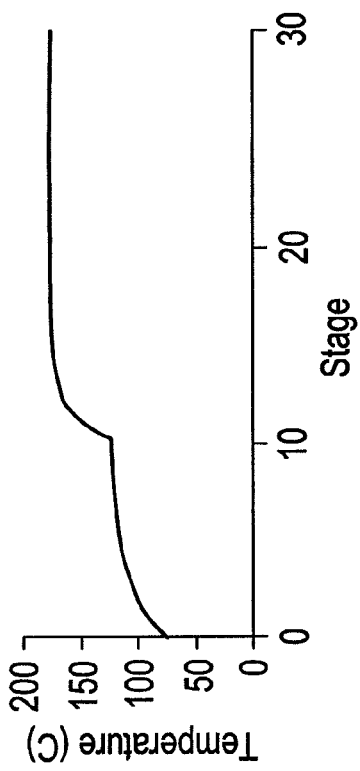
FIG. 5 is a graph showing the temperature profile of a $C_4$ fractionator according to the embodiment of Example 3.
Figure 6:
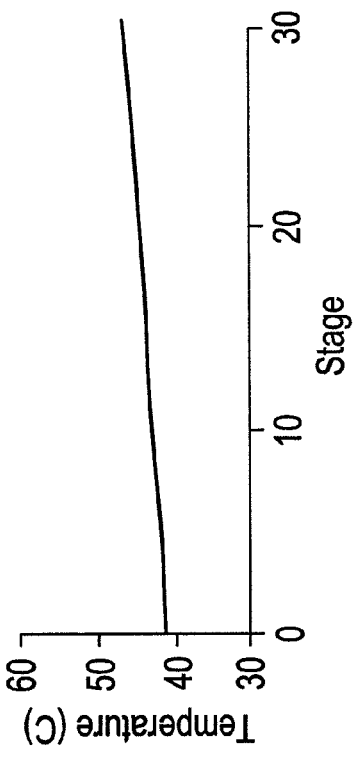
FIG. 6 is a graph showing the temperature profile of a depentanizer according to the embodiment of Example 3.

In the fractionator 168, comonomer grade hexene-1 (98.5 mol %) is taken as overhead product in line 171. There is no flow through line 172 and separator 176 is not in $C_6$ service. The hexene-1 product is removed in line 173, and a reflux line 175 returns to the tower with the hexene-1 product being removed in line 181. The bottoms hexene-2 and hexene-3 from tower 168 are recycled to the isomerization section in line 188. The contents of bottoms line 188 is mixed with the other hexene-2/hexene-3 recycle in line 122 from tower 114 to form line 126. The fractionator 168 operates at an overhead pressure of 50 kPa. Temperature profiles for the $C_6$ fractionation in fractionator 114 and fractionator 168 are shown in FIGS. 5 and 6, respectively.

As indicated above, the shared equipment from the batch process flowsheet is designed for operation in both $C_4$ and $C_6$ service. Depending on the type of equipment, this can be handled in different ways. Heat exchangers, for example, may have varying temperature approaches, but the heat exchanger surface area may be adjusted by using multiple shells. Reactors can be addressed by using multiple reactors. Because the fractionator towers cannot be handled in the same way as the heat exchangers or reactors, their design is chosen to remain fixed between services.

In order to use the same tower as both the $C_4$ and $C_6$ fractionator and to use the second tower as both the depentanizer and the $C_6$ fractionator, the tower sizing must be identical for the chosen flow rates. Because campaign operation allows for independent variation of the flow rates between $C_4$ and $C_6$ service, operating time can be used as a variable to adjust the flow rates such that a net yearly production of, e.g., 5 KTA hexene-1 is achieved. Using this approach, in one embodiment the $C_4$ process is operated for 2,000 hours to produce 2,696 kg/h hexene-3. 500 hours of downtime is provided to empty the fractionators and reactors in preparation for the $C_6$ run. Then, the $C_6$ process is operated for 5,333 hours, feeding 1,010 kg/h hexene-3 to produce 937 kg/h hexene-1. An additional 500 hours is allowed for the transition back to $C_4$ service. Operation at these flow rates yields the same tower diameter after choosing 100 theoretical stages for the $C_4/C_6$ fractionator, and likewise for 30 stages in the depentanizer/$C_6$ fractionator. An example of a process using the configuration of FIG. 2 is provided below as Example 2.

Overall, the shared use of the fractionator and isomerization system components in the batch process eliminates 35 of the 64 pieces of equipment from the continuous hexene-1 process. The continuous process has 2 complete superfractionator/isomerization reactor systems compared to just one for the campaign operation. The estimated reduction in total installed capital cost is about 35-45%. This makes campaign operation especially suited for smaller capacity installations.

Figure 4:
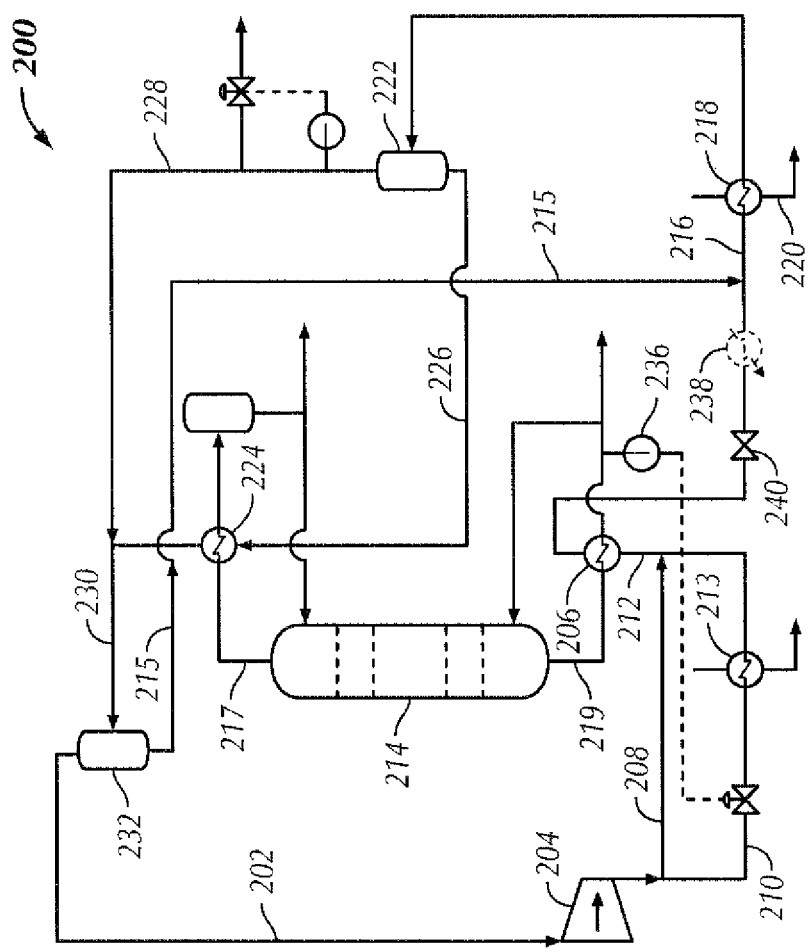
FIG. 4 is a process flow diagram showing the first fractionator with a closed loop heat pump system capable of operating with both the first isomerization effluent and the second isomerization effluent in the process of FIG. 3.

Referring now to FIG. 4, an embodiment is shown in which a closed-loop heat pump is used to even further improve the efficiency of the campaign process depicted in FIG. 3. The overall system is designated as 200. This system uses changes in pressure to adjust the boiling point of a heat transfer fluid within the temperature ranges of a fractionator's reboiler and condenser so that the fluid can be alternately condensed and vaporized, respectively, thus providing heat integration in place of conventional utilities such as refrigeration for condensing or steam for reboiler. The heat pump is associated with the fractionator 214. (A top line 217 and a bottoms line 219 are removed from the fractionator 214). The fluid begins the cycle as a vapor in vapor line 202. Vapor line 202 is compressed in a compressor 204 to a pressure where the temperature at which the vapor condenses is above the temperature of the reboiler 206. Compressed line 202 is divided into line 208 and line 210 and the two lines are recombined as line 212. Line 210 is cooled in a heat exchanger 213. The use of cooling water exchanger 213 allows for control of the duty in reboiler 206 by controlling the temperature and/or flow of the hot higher pressure vapor. In some cases the contents of line 210 are condensed in exchanger 213 and a 2 phase mixture fed to reboiler 206. This effectively limits the amount of heat transfer fluid that is condensed in the reboiler and thus the heat transferred to the reboiler. Line 212 is condensed in the reboiler 206. Controller 236 determines the split between lines 208 and 210. Line 212 is now in liquid phase.

At this point in the cycle the hot duty requirement of the reboiler is satisfied. The system must now satisfy the lower temperature duty of the tower condenser. Liquid in line 212 is let down in an expansion, controlled by the overhead vapor from expansion drum 222 to drop the boiling point below the temperature of the fractionator condenser 224. This reduces the temperature of the line as a portion of 212 is vaporized at the lower pressure. Line 212 is then combined with (optional) line 215 as line 216. Optionally, as described below, line 216 is cooled in heat exchanger 218 using cooling water line 220. Vapor is removed from drum 222 as line 228. Vapor is not sent to the condenser 224. The liquid is removed from drum 222 in line 226. Line 226 is then vaporized in the condenser 224 and after vaporization is combined with line 228 to form line 230. Line 230 passes through a knockout drum 232. The vapor in drum 232 is removed as line 202, which as mentioned above, is returned back to the compressor 204. Any small amount of liquid in drum 232 is removed in line 215, which is combined with the effluent from the expander 240 to form line 216.

To settle any difference in condenser and reboiler duty, an additional exchanger may be required within the loop to add or remove heat as necessary. In this particular campaign system, the condenser duty is greater than that of the reboiler, so heat exchanger 213 is placed at the compressor discharge in parallel with the reboiler to remove the difference in heat duty, allowing the heat pump fluid to fully condense in the reboiler 206. Heat exchanger 213 is the exchanger to remove "extra" duty from the loop based on the reboiler-condenser duty difference. Conversely, if the reboiler duty were greater, a heat exchanger 238 operated with steam instead of cooling water would be placed at the outlet of the expander 240 to have more of the fluid as vapor to separator 222 and thus feed lower amount of liquid as line 226 to vaporize in the condenser.

To avoid temperature crosses in the reboiler and condenser, a temperature difference of e.g., 3° C. can be used between the outlet temperatures of the process fluid, line 219 for example, and the heat pump, line 212. The compressor and expander discharge pressures can be considered fixed, set by the requirement to bring the heat pump fluid boiling point within the approach to the reboiler and condenser temperatures, respectively. Effectively, the work performed by the compressor is that required to undo the work of the expander, so the energy costs of the heat pump decrease as the temperature spread across the tower becomes smaller.

With the pressures in each portion of the heat pump cycle fixed and the condenser as the controlling duty, the inlet temperature to the condenser can be maximized in order to provide additional cooling capacity. In this case the cooling water heat exchanger 218 is used in the loop at the outlet of the expander to cool the line before entering the condenser 224. This is a low-cost method of reducing the circulation rate through the higher-cost compressor 204.

The working fluid for the heat pump used in a campaign mode of processing typically is a hydrocarbon or mixture of hydrocarbons such that the boiling point of that hydrocarbon or mixture falls between the boiling point of the first carbon number and the second carbon number. This differs from a conventional closed loop heat pump system that is operating on a single carbon number. There, the working fluid is selected based upon a single carbon number and typically has properties close to the hydrocarbon being separated. In one particular closed-loop system for campaign mode operation, n-butane is used as the circulating fluid and the heat pump is applied to one or both of the fractionators in the isomerization section operating in either $C_4$ or $C_6$ service. N-butane boils between the 1-butene overhead in one mode and the 3-hexene reboiler in the C6 service mode. Note also it is possible to use a mixture of fluids as the heat transfer fluid. In that case it is possible to adjust the composition to optimize the thermodynamic properties of the fluid mixture. The energy requirement of the heat pump is that to run the compressor, significantly less than the stand-alone tower due to the integration of reboiler and condenser heat duties. A closed loop applied to both towers would integrate both reboilers in series within the loop, then both condensers in series, adjusting the compressor and expander discharge pressures accordingly.

Variations in process parameters equipment sizing, etc. will depend upon the desired butene-1 purity. Very high purity butene-1 generally is not required to produce hexene-3 by autometathesis. The fractionation tower could be designed to produce for example 95% butene-1, with one part of the product going to autometathesis for lights, recycle and hexene-3, and another part going to a different fractionator to produce high purity butene-1 (polymer grade). In this case, both the depentanizer of the main example and the additional butene-1 fractionation could be used in campaign mode for hexene purification. It is noted that feed to autometathesis could be a tower side draw where overhead is the high purity butene-1.

A number of other methods of isomerization and metathesis can be applied and still maintain the important feature of the campaign process, which is shared equipment between $C_4$ and $C_6$ service. Further, additional processing steps and/or alternate feedstocks can be used. One non-limiting example of an alternative process would be to employ an additional metathesis reaction step involving the reaction of ethylene with butenes (ethenolysis). Depending upon the feed quality to the autometathesis step (the butene-2 content) some propylene and pentene-2 will be formed. A second autometathesis step involving the reaction between butene-1 and pentene-2 to yield propylene and hexene-3 could be included. This additional autometathesis step would, for example, involve line 75 or 82 of FIG. 2. Pentene-2 produced in reactor 52 can be sent to a second autometathesis reactor to make more hexene-3. A further example would be to incorporate the process of U.S. Pat. No. 4,709,115 (Jung et al, November 1987), where the metathesis step occurs in a catalytic distillation tower. In the campaign system, this variation would manifest itself as a catalytic depentanizer in $C_4$ service, with the catalyst replaced by inert beads to operate as $C_6$ fractionator in $C_6$ service.

The campaign processing scheme described herein also can be integrated with other processing units. For example, the campaign process can be integrated with a continuous conventional metathesis unit for producing propylene from the reaction of ethylene and butene-2. The conventional metathesis process typically feeds ethylene and a mixed $C_4$ raffinate stream containing butene-2, which can be the same $C_4$ feed raffinate stream as that used for the process in FIG. 1, to a metathesis reactor. Ethylene and propylene produced in the autometathesis step of the campaign operation is then sent to the fractionation system of the conventional metathesis unit. This effectively provides feed ethylene to the conventional metathesis reaction and provides propylene product. A recycle of $C_4$ is taken from the second separation step back to the reactor. To integrate the campaign process in FIG. 3, for example, the purge streams 118, 126, and 178 would be recycled to an appropriate disposition in the conventional metathesis process. Because this integration can use the same $C_4$ raffinate feed stream, a number of options are afforded. One option is that the total $C_4$ raffinate can remain constant, thus converting some propylene production in conventional metathesis to hexene-1 production in the campaign process. A second option is to maintain constant propylene production from the conventional metathesis process and "scale up" up the $C_4$ raffinate flow rate as required for butene-1 or hexene-1 production from the campaign process. Any intermediate combination of product flow rates from these options is also possible.

Two significant advantages exist in integrating the campaign process with conventional metathesis. First, all purge streams from the campaign process which would otherwise be lost to the cracking furnace or another low-value disposition can be recovered in the conventional process. In particular, the C2-C3 of stream 78 is ethylene that has been upgraded from the $C_4$ raffinate feed and greatly reduces the fresh ethylene requirement to the conventional metathesis unit. Second, it is possible to make use of the autometathesis reactor of the campaign process when it is idle in $C_6$ service. If additional $C_4$ raffinate and ethylene are available, they can be fed to the autometathesis reactor during the $C_6$ phase of the campaign process. Metathesis will produce additional propylene with no change of catalyst required. The additional propylene can be fed to the separation equipment of the conventional metathesis process and recovered. In this way, extra propylene production for a portion of the operating year is possible either to the limit of the separation equipment overdesign in a retrofit case, or to a desired amount in the case of a new integrated plant.

In a second integration example, a process for the production of olefins from methanol (MTO) produces a $C_4$-$C_6$ stream composed of linear olefins can be incorporated upstream. Similarly, processes that utilize ethylene oligomerization to produce linear alpha olefins have alpha olefin streams in even carbon numbers from $C_4$ through $C_{20}$+ can be incorporated. The campaign processing scheme in combination with metathesis can be used to adjust the carbon number distribution and thus maximize product value dependent upon market conditions. For example, a $C_{10}$ alpha olefin can be isomerized to a number of $C_{10}$ internal olefins using the isomerization step. The internal olefins can be then reacted with ethylene in a metathesis step to produce a range of lower carbon number alpha olefins. These can be separated and processed in campaign mode or alternately the isomerization/metathesis process used for a $C_{16}$ alpha olefin following operation with a $C_{10}$ alpha olefin feed.

The particular campaign system described includes two fractionators. One is used as a $C_4$ and $C_6$ fractionator and combined with the isomerization reactor. The second is used as a depentanizer and second $C_6$ fractionator. In one embodiment, the heat pump is placed on only the $C_4$/$C_6$ fractionator, with the depentanizer/$C_6$ fractionator using conventional utilities. Another embodiment involves use of a heat pump on the depentanizer/$C_6$ fractionator. In a further configuration a single heat pump loop passes through all fractionation towers. For a campaign process, this type of loop would operate on the $C_4$ fractionator and depentanizer during $C_4$ service, then on both $C_6$ fractionators during $C_6$ service, with possible sequences of reboiler-reboiler-condenser-condenser or reboiler-condenser-reboiler-condenser within the loop. Yet another configuration places one heat pump loop on each tower.

The embodiment of FIG. 2 shows a two-tower system for the fractionator following the isomerization system. This embodiment also can include the option of an integrated condenser/reboiler, with a heat pump on the "outer" exchangers. In this configuration, the tower pressures would be adjusted such that, for example, the condenser of the $C_4$ fractionator could be integrated with the reboiler of the depentanizer. The heat pump is then placed across the wider temperature range of the remaining exchangers. The integrated condenser/reboiler is possible with either the upstream or the downstream tower operating as the higher pressure tower.

In the embodiments described above in detail, one suitable circulating fluid to be used in the heat pump is n-butane. This fluid is useful because its boiling temperature is within range of the tower condenser and reboiler at appreciable pressure. Alternative heat pumps on this type of system can use a mixture of hydrocarbons or other fluids. Mixtures are particularly useful to extend the boiling range of the heat pump fluid for towers with wide temperature profiles, thus minimizing the difference between compressor and expander discharge pressures.

Heat pump loops with a constant circulation rate between $C_4$ and $C_6$ service are possible, with the compressor and/or expander discharge pressures relaxed to allow the use of some sensible heat when in the lower-duty service. A heat pump loop with or without heat exchanger 118, placed to provide additional cooling capacity at low cost (cooling water), is also feasible. In lieu of balancing the condenser and reboiler duties by removing heat in heat exchanger 113, a steam exchanger could be placed to add heat in the opposite portion of the loop.

The heat pump can be expanded to both fractionators of the batch system. This would result in heat integration of the condensers and reboilers of the $C_4$ fractionator and depentanizer, and the two $C_6$ fractionators. There can be a single heat pump loop or two separate loops having one heat pump on each tower.

One or more of the above variations may be used with an open-loop heat pump. An open-loop heat pump uses the tower overhead stream as the heat exchange fluid against the bottoms stream.

In another embodiment the pressures of the two fractionators can be adjusted such that, for example, the condenser of the $C_4$ fractionator is heat-integrated with the reboiler of the depentanizer. A heat pump can then be used on the reboiler of the $C_4$ fractionator and condenser of the depentenizer.

Some or all of the heat pump configurations described above may be employed using a mixture of fluids in the heat pump loop, which would provide a broader region of vaporization/condensing than a pure fluid. The required difference between compressor and expander discharge pressures, thus the compressor energy consumption, would be decreased. The batch system also presents the possibility of different fluids in the heat pump loop between $C_4$ and $C_6$ service, or a different fluid for each loop if two loops are used.

The following examples are included to illustrate certain features of the disclosed embodiments but are not intended to limit the scope of the description.

Example 1

Campaign Autometathesis Process Employing High-Selectivity WO3 Catalyst and an Integrated Two Tower Fractionation System A computerized simulation was conducted in which butene isomerization and autometathesis sections are operated as one unit, temporarily storing n-$C_6$ made in the autometathesis section in a process having the configuration shown in FIG. 2 with storage tank 84 being used but not 41. This was followed by $C_6$ isomerization operation utilizing the equipment used in the butene isomerization section. In this scheme, the entire set of $C_6$ isomerization equipment is avoided to reduce capital cost. In this Example, 5 KTA of polymer grade 1-hexene was produced in a campaign process. The butene feed used in shown in table 1 below.

TABLE 1

| C4 Feed to Autometathesis Process | |
|---|---|
| Component | Wt % |
| Iso-butane | 4.0 |
| n-butane | 16.1 |
| tr2-butene | 18.2 |
| 1-butene | 50.5 |
| iso-butene | 0.10 |
| cis2-butene | 11.1 |
| Total | 100.0 |
| Flow Rate, Kg/H | 14,900 |

In the campaign operation simulation, $C_4$ isomerization and autometathesis sections were operated for 2000 hours producing 3-hexene, which was temporarily stored in a storage tank for further isomerization to 1-hexene. After producing the 3-hexene for 2000 hours, $C_4$ isomerization and autometathesis operation were shut down and the distillation towers and reactors were emptied. The $C_6$ isomerization section was then operated for 5333 hours producing 1-hexene from the stored 3-hexene, utilizing the same equipment used in $C_4$ isomerization operation. Eliminating the $C_6$ isomerization equipment reduces capital cost. The particular hours of operations were chosen such that the interchangeability of the equipment was possible providing for a net yearly production of 5000 KTA of 1-hexene.

This process followed the same scheme as would be used in a continuous autometathesis process. The separation of 1-hexene from its isomers was the critical separation. In the continuous process, a two-tower design is used for this separation. The same two-tower separation system was used in the batch process for separation of 1-hexene from other $C_6$ compounds. Since this equipment was used in the butene isomerization, the same two-tower separation system applies to separation of 1-butene from 2-butene as well.

The raffinate II feed composition is given in Table 1. The 1-butene content in the $C_4$ feed is higher than the equilibrium butene ratio at 650 F, the operating temperature of the $C_4$ isomerization reactor (feed B1/B2=2.8, equilibrium B1/B2 at 650 F=0.28). Hence the raffinate II feed was sent to the $C_4$ separation tower system to separate 1-butene prior to entering the butene isomerization reactor.

The bottom product from the $C_4$ separation contained mainly 2-butenes and n-butane. This bottom product stream was recycled to the isomerization reactor to increase n-butene utilization. A small purge was removed from this recycle stream to control the build-up of the inerts, n-butane and iso-butane. The isomerization reactor feed exchanged heat with the hot reactor product. The reactor feed was further heated to the reaction temperature inside a fuel-fired furnace and entered the reactor. The reactor was operated at 650 Deg. F. and 117 psia. The catalyst was MgO tablets. Feed ratios and 2-butene conversion data for the isomerization reactor are shown below on Table 2. The reaction product was sent to the butene separation system. The $C_4$ isomerization reactor and separation tower were used during the $C_6$ isomerization operation as well.

The C4 separation system consisted of a two tower system. The condenser of one tower is used to reboil the second tower. The two towers are operated at different pressures to allow for this exchange. Splitting the feed with a portion to each tower reduces energy consumption while balancing the duties for each tower. The first fractionator had 80 stages and second fractionator had 70 stages. The raffinate II feed entered second tower at stage 24. The butene isomerization reactor product was split. One portion entered the first tower at stage 15 and other portion entered the second tower at stage 48. The distillate product from first tower, concentrated in 1-butene entered the second tower at stage 30. By adjusting the vapor feed split ratio and operating pressures of the towers, energy exchange between the tower 1 condenser and tower 2 re-boiler was made possible. The final distillate product was 90 mol % 1-butene, which was sent to the autometathesis section for further processing. The 1-butene product stream contained iso-butane (5.1 wt %), n-butane (3.8 wt %), tr2-butene (1.2 wt %) and iso-butene (0.13 wt %). If required, monomer grade 1-butene (99 wt %) could also be produced from this separation system. Details of the separation tower are given in Table 5 below.

In the second processing step but still operating in the C4 mode, 1-butene from the butene isomerization/separation system was sent to the autometathesis section to produce n-hexenes. In this section, 1-butene feed was mixed with recycled 1-butene from the separators and exchanged heat with the hot reactor product. The reactor feed was further heated to the reaction temperature inside a fuel-fired furnace and entered the reactor. The autometathesis reactor operated at 600 F and 275 psia. The catalyst was WO3 on high-purity silica. Inside this reactor, 1-butene reacted with itself to produce ethylene and 3-hexene. Side reactions between 1-butene and 2-butenes producing propylene and 2-pentenes also occurred. Moreover, isobutylene reacted with 1-butene to produce ethylene and 2-methyl-2-pentene (i-$C_6$ olefin, BP=67.3 deg C.). The other possible isobutylene reactions were determined to be insignificant. The production of i-$C_6$ olefin in the autometathesis reactor is undesirable since it affects the purity of 1-hexene product. Hence the isobutylene content in the raffinate II feed was kept very low. A small amount of C7 and C8 was also produced by other metathesis reactions. Recycle, conversion, and reaction product composition data are shown on Table 3.

The autometathesis reaction products were separated in the depentenizer. The 3-hexene was recovered in the depentenizer tower as bottom product and sent to the storage tank for use in the C6 mode step of the campaign process. The i-$C_6$ olefins, C7 and C8 produced inside the autometathesis reactor were also carried along with the 3-hexene. The distillate from the depentenizer was sent to the depropenizer for further separation. The lighter components, ethylene and propylene were recovered as distillate and sent to product recovery in the ethylene plant. The unconverted 1-butene was recovered as the bottom product and recycled to the autometathesis reactor to improve butene utilization. A side-draw stream was purged from the depropylenizer to remove the inerts, iso-butane and n-butane from the autometathesis system. The details of the separation tower are shown below.

At the completion of the $C_4$ isomerization and autometathesis run, the process was shut down. The reactors and distillation towers were emptied in preparation for the $C_6$ isomerization run. The $C_6$ isomerization operation was then conducted as shown in the process flow diagram.

The hexene isomerization section consisted of a hexene isomerization reactor and hexene separation system, and the same equipment as was used for $C_4$ processing was employed. The 3-hexene from the storage tank was mixed with recycled 2-hexenes and 3-hexenes from the $C_6$ separation system and exchanged heat with the hot isomerization reactor product. The isomerization reactor feed was further heated to the reaction temperature inside a fuel-fired furnace and entered the reactor. The reactor operated at 650 F and 56 psia. The catalyst was MgO tablets. The reactor product was an equilibrium mixture of 1-hexene, 2-hexenes and 3-hexenes including the cis-trans isomers. This product mixture was separated in the hexene separation system to produce polymer grade 1-hexene as distillate product. (The two-tower separation system with energy integration was explained previously.) The bottom product, 2-hexenes and 3-hexenes were recycled to the isomerization reactor. A small purge was taken from the separation system to remove the heavy components from the $C_6$ isomerization system. The details of the separation tower are given below in Table 6.

The 2-methyl-2-pentene from the autometathesis reactor was also carried over to the hexene isomerization section where the isomerization activity of the MgO catalyst produced its isomers: 2-methyl-1-pentene, 4-methyl-1-pentene, 4-methyl-cis-2-pentene and 4-methyl-trans-2-pentene. Since the boiling point of all i-$C_6$ except the 2-methyl-2-pentene are lower than 1-hexene, any i-$C_6$ produced in the autometathesis reactor ends up with the 1-hexene product.

TABLE 2

| Butene Isomerization Reactor | |
|---|---|
| Rx Operating Temp, F. | 650 |
| Rx Operating Pr, Psia | 117 |
| Catalyst | MgO tablets |
| Rx Feed B2/B1 ratio | 49 |
| Rx Prod B2/B1 ratio | 3.6 |
| 2-Butene conversion, % | 21.7 |

TABLE 3

| Autometathesis Reactor | |
|---|---|
| Rx Operating Temp, F. | 600 |
| Rx Operating Pr, Psia | 275 |
| Catalyst | WO3 on high purity silica |
| Rx Feed B1/B2 ratio | 96.2 |
| B1 Conversion, mol % | 46.2 |
| Molar Selectivity, % | |
| Ethylene | 40.53 |
| Propylene | 12.22 |
| Pentene | 0.02 |
| n-hexene | 46.48 |
| i-hexene | 0.15 |
| C7 and C8 | 0.60 |

The autometathesis reactor performance was based on experimental data for high selectivity WO3 catalyst. This information was incorporated into the HYSYS simulation. The conversion and selectivity were determined for the autometathesis reactor feed given in Table 10. The autometathesis selectivity for the main reaction ($C_2$+$C_6$) was 87.01. The selectivity for the side reactions ($C_3$+$C_5$) was 12.37. The selectivity for the isobutylene reaction with 1-butene was 0.15. A small amount of C7 and C8 was also formed in the autometathesis reactor.

TABLE 4

Hexene Isomerization Reactor

| | |
|---|---|
| Rx Operating Temp, F. | 650 |
| Rx Operating Pr, Psia | 56 |
| Catalyst | MgO tablets |
| Rx Feed (2-hex + 3-hex)/1-hex ratio | 63.36 |
| Rx Prod (2-hex + 3-hex)/1-hex ratio | 10.6 |
| 1-Hex Prod Composition, mol % | 8.3 |

The $C_6$ isomerization reactor performance was obtained from the correlation of experimental data. This correlation was incorporated into the HYSYS simulation.

TABLE 5

Specifications of the Separation Columns in C4 Isomerization and Autometathesis

| Parameter | Depropenizer | Depentenizer | Butene Splitter1 | Butene Splitter2 * |
|---|---|---|---|---|
| Number of Stages | 15 | 40 | 80 | 70 |
| Feed Tray (# from top) | 5 | 20 | 15 | 24, 30, 48 |
| condenser P, Kpa | 2200 | 1600 | 700 | 530 |
| re-boiler P, Kpa | 2300 | 1800 | 750 | 550 |
| Top Spec | 1.5 mol % 1-C4 in distillate | 0.1 mol % n-$C_6$ in distillate | 40 mol % 1-butene in distillate | 90 mol % 1-butene in distillate |
| Bottom Spec | 0.5% propylene in bottom | 0.01 mol % n-$C_5$ in bottom product | 0.5 mol % 1-butene in bottom product | 1 mol % 1-butene in bottom prod |
| Other Specs | | Top vent = 15 kmol/h Side draw = 23 kmol/h Interstage cooling at stage 3 = 1000 KW | | |
| Note | | Bottom product is 98.5 wt % n-$C_6$ | | |

TABLE 6

Specifications of the separation columns in $C_6$ isomerization

| Parameter | $C_6$ Splitter1 | $C_6$ Splitter2 * |
|---|---|---|
| Number of Stages | 80 | 70 |
| Feed Tray (# from top) | 25 | 40, 60 |
| condenser P, Kpa | 207 | 117 |
| re-boiler P, Kpa | 241 | 138 |
| Top Spec | 60 mol % 2&3 hexene in distillate | 1.2 mol % 2&3 hexene in distillate |
| Bottom Spec | 1 mol % 1-hexene in side-draw product | 2.5 mol % 1-hexene in bottom prod |
| Other Specs | 45 mol % C7 & C8 in bottom product | |
| Note | Side-draw from stage 74 | |

The material balance for the batch case, producing 5 KTA of polymer grade 1-hexene is given below. The material balance summary as well compositions of key streams are given in the following tables.

TABLE 7

Overall material balance for C4 Isomerization and Autometathesis (2000 hours operation)

| | MTA |
|---|---|
| Feed | |
| C4 Feed | 12,000 |
| Total Feed | 12,000 |
| Products | |
| C2/C3 to cracker | 1,852 |
| Depropenizer side draw | 2,120 |

TABLE 7-continued

Overall material balance for C4 Isomerization and Autometathesis (2000 hours operation)

| | MTA |
|---|---|
| C4 purge | 2,637 |
| Depentenizer Bottom | 5,391 |
| Total Products | 12,000 |

TABLE 8

Overall material balance for $C_6$ Isomerization (5333 hours operation)

| | MTA |
|---|---|
| Feed | |
| $C_6$ Feed | 5,391 |
| Total Feed | 5,391 |
| Products | |
| Hexane-1 Prod | 5,026 |
| $C_6$ purge | 205 |
| $C_6$+ Purge | 160 |
| Total Products | 5,391 |

TABLE 9

Material balance for the butene isomerization section (2000 hours operation)

| Component, wt % | C4 Feed | C4 recycle | C4 Isomerization Feed | C4 Isomerization Prod | C4 Purge | B1 to Autometathesis |
|---|---|---|---|---|---|---|
| Iso-butane | 4.04 | 0.0 | 0.0 | 0.0 | 0.0 | 5.2 |
| n-butane | 16.14 | 61.3 | 61.3 | 61.3 | 61.3 | 3.5 |
| Tr2-butene | 18.17 | 22.6 | 22.6 | 17.8 | 22.6 | 1.3 |
| 1-butene | 50.45 | 0.70 | 0.70 | 8.5 | 0.70 | 89.7 |
| Iso-butene | 0.10 | 0.0 | 0.0 | 0.0 | 0.0 | 0.13 |
| Cis2-butene | 11.10 | 15.4 | 15.4 | 12.3 | 15.4 | 0.10 |
| Total, wt % | 100 | 100 | 100 | 100 | 100 | 100 |
| Flow, Kg/h | 6000 | 15165 | 15165 | 15165 | 1318 | 4682 |

TABLE 10

Material balance for the autometathesis section (2000 hours operation)

| Component, wt % | B1 to Autometathesis | B1 Recycle | Auto. Rctr. Feed | Auto. Rctr. Prod | C2/C3 to Cracker | Depropenizer sidedraw | Depentenizer bottom |
|---|---|---|---|---|---|---|---|
| Ethylene | 0.0 | 0 | 0 | 6.0 | 62.4 | 17.1 | |
| Propylene | 0.0 | 0.4 | 0.2 | 2.9 | 16.7 | 17.1 | |
| Iso-butane | 5.2 | 20.0 | 14.6 | 14.6 | 6.3 | 18.0 | |
| n-butane | 3.5 | 26.1 | 17.9 | 17.9 | 3.7 | 12.7 | |
| Tr2-butene | 1.3 | 0.2 | 0.6 | 0.2 | 0 | 0.10 | |
| 1-butene | 89.7 | 48.0 | 63.3 | 34.0 | 10.9 | 34.5 | |
| Iso-butene | 0.13 | 0.04 | 0.07 | 0.03 | 0 | 0.04 | |
| Cis2-butene | 0.10 | 0.04 | 0.06 | 0.02 | 0 | 0.0 | |
| n-Pentene | 0.0 | 5.1 | 3.2 | 3.2 | 0 | 0.41 | |
| 3-hexene | 0.0 | 0.2 | 0.13 | 20.8 | 0 | 0.0 | 98.2 |
| i-$C_6$ | 0.0 | 0.0 | 0.0 | 0.07 | 0 | 0.0 | 0.3 |
| C7 & C8 | 0.0 | 0.0 | 0.0 | 0.32 | 0 | 0.0 | 1.5 |
| Total, wt % | 100 | 100 | 100 | 100 | 100 | 100 | 100 |
| Flow, Kg/h | 4682 | 8,096 | 12,799 | 12,799 | 9,26 | 1,060 | 2696 |

TABLE 11

Material balance for the hexene isomerization section (5333.3 hours operation)

| Component, wt % | $C_6$ Recycle | $C_6$ Isomerization Feed | $C_6$ Isomerization Prod | 1-hexene Prod | $C_6$ Purge | $C_7$+ Purge |
|---|---|---|---|---|---|---|
| 1-hexene | 1.7 | 1.6 | 8.4 | 98.5 | 1.7 | 0.2 |
| Tr2-hexene | 46.1 | 50.0 | 42.9 | 0.46 | 46.1 | 23.6 |
| Tr3-hexene | 21.5 | 19.9 | 20.0 | 0.35 | 21.5 | 8.6 |
| Cis2-hexene | 23.1 | 21.4 | 21.5 | 0 | 23.1 | 16.3 |
| Cis3-hexene | 7.1 | 6.6 | 6.6 | 0.4 | 7.1 | 2.4 |
| i-$C_6$ | 0.1 | 0.1 | 0.1 | 0.33 | 0.1 | 0.1 |
| C7 & C8 | 0.44 | 0.5 | 0.5 | 0.0 | 0.44 | 48.8 |
| Total, wt % | 100 | 100 | 100 | 100 | 100 | 100 |
| Flow, Kg/h | 12,645 | 13,656 | 13,656 | 942 | 38 | 30 |

A comparison of the overall material balances for a continuous process at 50 KTA using the same feed composition as the batch process of this example shows that the major streams scale down linearly for the campaign case. Some minor difference in the C2/C3 to cracker and depropenizer side-draw were noticed, and arose from the operation of the depropenizer tower.

The energy balance for the campaign case study, producing 5 KTA of polymer grade 1-hexene is provided below. The energy balance for the butene isomerization section, autometathesis section and hexane isomerization sections are shown. In Table 12 there are shown two balances. The "Before Exchange" tabulation lists the duties for each of the tower reboilers or condensers in the C4 or C6 modes. The "After Exchange" tabulation simply subtracts the common duty from the "before Exchange" tabulation. For example in the C4 Isom mode, Tower 1 condenser has a duty of 6733 KW and the tower 2 reboiler has a duty of 6670 KW. Since these are exchanged against each other, the after exchange duty is the difference (63 KW).

TABLE 12

Energy balance summary for the campaign process

|  | $C_4$ Isom (2000 hours) | Autometathesis (2000 hours) | $C_6$ Isom (5333 hours) | Total |
|---|---|---|---|---|
| BEFORE EXCHANGE |  |  |  |  |
| Feed vaporizer (LPS), KW | 1626 | 980 | 1408 |  |
| Feed Heater (fuel), KW | 130 | 430 | 126 |  |
| Tower 1 Condenser duty (CW), KW | 6733 (a) | © 1000, 71* | 5876 (a) |  |
| Tower 1 Re-boiler duty (LPS), KW | 5437 | 1500 | 4801 |  |
| Tower 2 Condenser duty (CW), KW | 7843 | 2959 | 6414 |  |
| Tower 2 Re-boiler duty (LPS), KW | 6670 (a) | 1427** | 5853 (a) |  |
| Pump, power, KW | 98 | 50 | 90 |  |
| AFTER EXCHANGE |  |  |  |  |
| Feed vaporizer (LPS), KW | 1626 | 980 | 1408 |  |
| Feed Heater (fuel), KW | 130 | 430 | 126 |  |
| Tower 1 Condenser duty (CW), KW | 63 (a) | © 1000, 71* | 23 (a) |  |
| Tower 1 Re-boiler duty (LPS), KW | 5437 | 1500 | 4801 |  |
| Tower 2 Condenser duty (CW), KW | 7843 | 2959 | 6414 |  |
| Tower 2 Re-boiler duty (LPS), KW | 0 (a) | 1427** | 0 (a) |  |
| Pump, power, KW | 98 | 50 | 90 |  |
| Total Utility After Exchange |  |  |  |  |
| FUEL, KW | 130 | 430 | 126 |  |
| −5 REF, KW |  | 71 |  |  |
| CW, KW | 7906 | 3959 | 6437 |  |
| LPS, KW | 7063 | 2480 | 6209 |  |
| HPS, KW |  | 1427 |  |  |
| POWER, KW | 98 | 50 | 90 |  |
| Total Utility After Exchange (8000 Hour Basis) |  |  |  |  |
| FUEL, KW |  |  |  | 224 |
| −5 REF, KW |  |  |  | 17.8 |
| CW, KW |  |  |  | 7,258 |
| LPS, KW |  |  |  | 6,525 |
| HPS, KW |  |  |  | 357 |
| POWER, KW |  |  |  | 97 |
| FUEL, MKCAL/H |  |  |  | 0.19 |
| −5 REF, MKCAL/H |  |  |  | 0.015 |
| CW, MKCAL/H |  |  |  | 6.22 |
| LPS, MKCAL/H |  |  |  | 5.59 |
| HPS, MKCAL/H |  |  |  | 0.306 |
| POWER, MKCAL/H |  |  |  | 0.083 |

Note:
1. In Autometathesis, tower1 is a depropylenizer and tower 2 is a depentenizer. (i) *depropenizer condenser is −5 deg refrigerant. (ii) **depentenizer re-boiler is HPS. (iii) © 1000 KW CW interchange on DEC3 to reduce the refrigerant duty.
2. In $C_4$ Isom, tower 1 is BS1 - higher pressure and tower 2 is BS2 - lower pressure tower.
3. In $C_6$ Isom, tower 1 is HS1 - higher pressure and tower 2 is HS2 - lower pressure tower.
4. The energy integration in two-tower system was explained previously.
(a). exchange between BS1/HS1 condenser and BS2/HS2 re-boiler in $C_4/C_6$ isomerization system. This is the exchange for the internal condenser/reboiler system of the two tower split feed system The energy balance for the batch process given in Table 12 above can be compared to the energy balance for a continuous process using the same equipment and feed composition, and is shown below on Table 13.

TABLE 13

Energy balance summary for a continuous processing autometathesis case - before and after energy exchange

|  | $C_4$ Isom | Automet | $C_6$ Isom | Total |
|---|---|---|---|---|
| Feed vaporizer (LPS), KW | 4141 | 2447 | 9747 |  |
| Feed Heater (fuel), KW | 971 | 1088 | 1816 |  |
| Tower 1 Condenser duty (CW), KW |  | © 2500, 80* | 24920 (a) |  |
| Tower 1 Re-boiler duty (LPS), KW |  | 3756 | 19810 |  |
| Tower 2 Condenser duty (CW), KW | 35110 | 7551 | 31070 (b) |  |
| Tower 2 Re-boiler duty (LPS), KW | 28400 (b) | 3682** | 23980 (a) |  |
| Pump, power, KW | 104 | 50 | 165 |  |
| Total Utility Before Energy Exchange |  |  |  |  |
| FUEL, KW |  |  |  | 3,875 |
| −5 REF, KW |  |  |  | 80 |
| CW, KW |  |  |  | 101,151 |
| LPS, KW |  |  |  | 92,281 |
| HPS, KW |  |  |  | 3,682 |
| POWER, KW |  |  |  | 319 |
| FUEL, MKCAL/H |  |  |  | 3.32 |
| −5 REF, MKCAL/H |  |  |  | 0.07 |
| CW, MKCAL/H |  |  |  | 86.7 |

TABLE 13-continued

Energy balance summary for a continuous processing automethathesis case - before and after energy exchange

| | $C_4$ Isom | Automet | $C_6$ Isom | Total |
|---|---|---|---|---|
| LPS, MKCAL/H | | | | 79.10 |
| HPS, MKCAL/H | | | | 3.16 |
| POWER, MKCAL/H | | | | 0.27 |
| Total Utility After Energy Exchange | | | | |
| FUEL, KW | | | | 3,875 |
| −5 REF, KW | | | | 80 |
| CW, KW | | | | 48,771 |
| LPS, KW | | | | 39,901 |
| HPS, KW | | | | 3,682 |
| POWER, KW | | | | 319 |
| FUEL, MKCAL/H | | | | 3.32 |
| −5 REF, MKCAL/H | | | | 0.07 |
| CW, MKCAL/H | | | | 41.80 |
| LPS, MKCAL/H | | | | 34.20 |
| HPS, MKCAL/H | | | | 3.16 |
| POWER, MKCAL/H | | | | 0.27 |

Note:
1. In Automet, tower1 is a depropenizer DeC3)and tower 2 is a depentenizer (DeC5). (i) *-depropenizer condenser is −5 deg refrigerant. (ii) **- DEC5 re-boiler is HPS. (iii) © 2500 KW CW interchange on DEC3 to reduce the refrigerant duty.
2. In $C_6$ Isom, tower1 is HS1 - higher pressure and tower 2 is HS2 - lower pressure tower.
3. The energy integration was explained in table.17. It is noted in table.22 as well. (a) exchange between HS1 condenser and HS2 re-boiler in $C_6$ isom system. (b) exchange between HS2 condenser in $C_6$ isom and BS re-boiler in $C_4$ Isom.

It is noted that energy integration reduced the total cooling water requirement by 53% and LPS requirement by 56%.

The utility usage scales down linearly in the batch case except for the cooling water and LPS. In the batch operation, an energy efficient two-tower $C_6$ separation system is employed. However, the energy integration between $C_6$ isomerization and $C_4$ isomerization towers could not practiced due to the batch operation. This increased the CW and LPS usage in the batch process. It appears that the savings in capital cost more than offset the increased utility cost. Details can be found in the economic evaluation of the processes.

Example 2

Campaign Autometathesis Process

In the previous Example, a campaign process to produce 5 KTA of 1-hexene was discussed. In this process, the improvements over Example 1 are:
1. In the $C_4$ isomerization process, one distillation tower with 100 stages replaced two-tower system with total of 150 stages.
2. In the autometathesis section, the depropylenizer tower was replaced by a gas-liquid separator.
3. In the $C_6$ isomerization process, one distillation tower with 100 stages (same used in $C_4$ isom) replaced two-tower system with total of 150 stages. The depentanizer tower acted as the second distillation tower.

Elimination of the two-tower separation system impacted the energy usage in the process. Since energy integration was not done, the utility consumption increased. Furthermore, the elimination of depropylenizer tower resulted in increased purge flows. However, economic analysis showed that capital cost savings more than offset the increased utility cost. In this case study, 5 KTA of polymer grade 1-hexene was produced in an improved campaign process.

The butene feed used in this study is given in Table 1 above. The process flow scheme is shown in FIG. 3.

The raffinate II feed was sent to the $C_4$ separation tower to separate 1-butene prior to the butene isomerization reactor. A single-tower separation replaced the energy integrated two-tower system in FIG. 2 in order to eliminate one distillation tower and associated equipment.

In the autometathesis section, a gas-liquid separator replaced the depropylenizer tower. The depentenizer vapor distillate was cooled and sent to a gas-liquid separator. The lighter components, ethylene and propylene were recovered as vapor and sent to product recovery in the ethylene plant. The unconverted 1-butene was recovered in the liquid product and recycled to the autometathesis reactor to improve butene utilization. Most of the autometathesis equipment was used only during autometathesis operation, except for the depentanizer tower that was used in $C_6$ isomerization operation as well.

At the completion of $C_4$ isomerization and autometathesis run, the process was shut down. The reactors and distillation towers were emptied in preparation for the $C_6$ isomerization run. The $C_6$ isomerization operation was conducted employing the same equipments as shown in FIG. 3.

In the $C_6$ isomerization section, the feed mixture was separated using two distillation towers as shown in the flow diagram. The first distillation tower (butene splitter) produced 93% hexene-1 distillate product. The bottom product, 2-hexenes and 3-hexenes were recycled to the isomerization reactor. A small bottom purge was taken from this distillation tower to remove the heavy components, $C_7$ and $C_8$ from the $C_6$ isomerization system. The depentenizer acted as the second hexene distillation tower that produced polymer grade hexene-1 from 93% hexene-1 feed. The specification for the depentenizer was 65 mol % 1-hexene in the bottom product. This specification was relaxed so that 2&3-hexenes were carried to bottom product allowing polymer grade 1-hexene to be made as the distillate product. The flow rate of this product was low as compared to the distillate product. The depentenizer bottom was mixed with the other bottom product and recycled to the $C_6$ isomerization reactor. By employing the depentenizer as the second hexene splitter, the number of stages in the first hexene splitter was reduced from 150 to 100. The details are given in following tables.

TABLE 14

Butene Isomerization Reactor

| Rx Operating Temp, F. | 650 |
|---|---|
| Rx Operating Pr, Psia | 117 |
| Catalyst | MgO tablets |
| Rx Feed B2/B1 ratio | 203 |
| Rx Prod B2/B1 ratio | 3.6 |
| 2-Butene conversion, % | 21.7 |

TABLE 15

Autometathesis Reactor

| Rx Operating Temp, F. | 600 |
|---|---|
| Rx Operating Pr, Psia | 275 |
| Catalyst | WO3 on high purity silica |
| Rx Feed B1/B2 ratio | 33.6 |
| B1 Conversion, mol % | 36.2 |
| Molar Selectivity, % | |
| Ethylene | 40.0 |
| Propylene | 12.50 |
| Pentene | 0.83 |
| n-hexene | 45.7 |

TABLE 15-continued

Autometathesis Reactor

| | |
|---|---|
| i-hexene | 0.15 |
| C7 and C8 | 0.82 |

The autometathesis reactor performance was based on experimental data for high selectivity WO3 catalyst. This information was incorporated into the HYSYS simulation. The conversion and selectivity were determined for the autometathesis reactor feed given in Table 21. The autometathesis selectivity for the main reaction ($C_2+C_6$) was 85.7. The selectivity for the side reactions ($C_3+C_5$) was 13.3. The selectivity for the isobutylene reaction with 1-butene was 0.15. A small amount of C7 and C8 were also formed in the autometathesis reactor.

TABLE 16

Hexene Isomerization Reactor

| | |
|---|---|
| Rx Operating Temp, F. | 650 |
| Rx Operating Pr, Psia | 56 |
| Catalyst | MgO tablets |
| Rx Feed (2-hex + 3-hex)/1-hex ratio | 43.4 |
| Rx Prod (2-hex + 3-hex)/1-hex ratio | 10.9 |
| 1-Hex Prod Composition, mol % | 8.4 |

TABLE 17

Specifications of the separation columns

| Parameter | Butene Splitter | Depentenizer | Hexene Splitter1 | Hexene Splitter2* |
|---|---|---|---|---|
| Number of Stages | 100 | 30 | 100 | 30 |
| Feed Tray (# from top) | 20, 45 | 10 | 65 | 10 |
| condenser P, Kpa | 570 | 1200 | 120 | 110 |
| re-boiler P, Kpa | 600 | 1280 | 140 | 120 |
| Top Spec | 90 mol % 1-$C_4$ in distillate | RR = 1.0 | 7 mol % 2&3-hex in distillate | 1.2 mol % 2&3-hex in distillate |
| Bottom Spec | 0.2% 1-$C_4$ in bottom | 0.98 mol % $C_6$ in bottom | 1.5 mol % 1-$C_6$ in side-draw | 65 mol % 1-hex in bottom prod |
| Other Specs | | | 45 mol % C7 and C8 in bottom product | |
| Note | | | | |

*Note: During the $C_6$ Isomerization batch operation, the depentenizer tower acts as the second hexene splitter, allowing reduced number of stages on the first separation tower.

The material balance for the batch case study, producing 5 KTA of polymer grade 1-hexene is given below. The material balance summary as well compositions of key streams are given in the following tables.

TABLE 18

Overall material balance for $C_4$ Isomerization and Autometathesis (2000 hours operation)

| | MTA |
|---|---|
| Feed | |
| $C_4$ Feed | 12,250 |
| Total Feed | 12,250 |
| Products | |
| C2/C3 to cracker | 4,240 |
| $C_4$ purge | 2,617 |
| Depentenizer Bottom | 5,393 |
| Total Products | 12,250 |

TABLE 19

Overall material balance for $C_6$ Isomerization (5333 hours operation)

| | MTA |
|---|---|
| Feed | |
| $C_6$ Feed | 5,387 |
| Total Feed | 5,387 |
| Products | |
| Hexane-1 Prod | 4,997 |
| $C_6$ purge | 225 |
| $C_6$+ Purge | 165 |
| Total Products | 5,387 |

TABLE 20

Material balance for the butene isomerization section (2000 hours operation)

| Component, wt % | $C_4$ Feed | $C_4$ recycle | $C_4$ Isomerization Feed | $C_4$ Isomerization Prod | $C_4$ Purge | B1 to Autometathesis |
|---|---|---|---|---|---|---|
| Iso-butane | 4.04 | 0.0 | 0.0 | 0.0 | 0.0 | 5.1 |
| n-butane | 16.14 | 61.8 | 61.8 | 61.8 | 61.8 | 3.7 |
| Tr2-butene | 18.17 | 22.6 | 22.6 | 17.6 | 22.6 | 1.2 |
| 1-butene | 50.45 | 0.20 | 0.20 | 8.4 | 0.20 | 89.7 |

TABLE 20-continued

Material balance for the butene isomerization section (2000 hours operation)

| Component, wt % | $C_4$ Feed | $C_4$ recycle | $C_4$ Isomerization Feed | $C_4$ Isomerization Prod | $C_4$ Purge | B1 to Autometathesis |
|---|---|---|---|---|---|---|
| Iso-butene | 0.10 | 0.0 | 0.0 | 0.0 | 0.0 | 0.13 |
| Cis2-butene | 11.10 | 15.3 | 15.3 | 12.2 | 15.3 | 0.10 |
| Total, wt % | 100 | 100 | 100 | 100 | 100 | 100 |
| Flow, Kg/h | 6125 | 15029 | 15029 | 15029 | 1308 | 4817 |

TABLE 21

Material balance for the autometathesis section (2000 hours operation)

| Component, wt % | Butene-1 to Autometathesis | Butene-1 Recycle | AR Feed | AR Prod | C2/C3 to Cracker | Depropenizer sidedraw | Depentenizer bottom |
|---|---|---|---|---|---|---|---|
| Ethylene | 0.0 | 5.7 | 4.4 | 8.0 | 36.3 | 18.0 | |
| Propylene | 0.0 | 10.3 | 7.9 | 9.6 | 17.0 | 17.10 | |
| Iso-butane | 5.1 | 17.1 | 14.4 | 14.4 | 11.7 | 17.50 | |
| n-butane | 3.7 | 15.6 | 12.9 | 12.9 | 8.4 | 13.2 | |
| Tr2-butene | 1.2 | 1.3 | 1.3 | 1.1 | 0.70 | 0.10 | |
| 1-butene | 89.7 | 38.4 | 50.2 | 32.0 | 23.8 | 33.90 | |
| Iso-butene | 0.10 | 0.0 | 0.10 | 0.0 | 0.0 | 0.0 | |
| Cis2-butene | 0.10 | 0.2 | 0.20 | 0.20 | 0.10 | 0.0 | |
| n-Pentene | 0.0 | 9.7 | 7.5 | 7.6 | 1.9 | 0.40 | |
| 3-hexene | 0.0 | 1.7 | 1.3 | 13.8 | 0.10 | 0.0 | 97.7 |
| i-$C_6$ | 0.0 | 0.0 | 0.0 | 0.04 | 0.0 | 0.0 | 0.32 |
| C7 & C8 | 0.0 | 0.0 | 0.0 | 0.25 | 0.0 | 0.0 | 2.0 |
| Total, wt % | 100 | 100 | 100 | 100 | 100 | 100 | 100 |
| Flow, Kg/h | 4817 | 16,216 | 21,033 | 21,033 | 2,120 | | 2696 |

TABLE 22

Material balance for the hexene isomerization section (5333.3 hours operation)

| Component, wt % | $C_6$ Recycle | $C_6$ Isomerization Feed | $C_6$ Isomerization Prod | HS1 Prod | 1-hexene Prod | $C_6$ Purge | $C_7+$ Purge |
|---|---|---|---|---|---|---|---|
| 1-hexene | 2.4 | 2.2 | 8.4 | 92.7 | 98.5 | 2.4 | 0.3 |
| Tr2-hexene | 45.9 | 49.5 | 43.0 | 2.8 | 0.4 | 45.9 | 22.4 |
| Tri-hexene | 21.4 | 20.0 | 20.1 | 2.0 | 0.3 | 21.4 | 9.5 |
| Cis2-hexene | 23.0 | 21.5 | 21.6 | 0.0 | 0.0 | 23.0 | 16.1 |
| Cis3-hexene | 7.1 | 6.6 | 6.6 | 2.2 | 0.5 | 7.1 | 2.8 |
| i-$C_6$ | 0.07 | 0.08 | 0.08 | 0.3 | 0.33 | 0.07 | 0.1 |
| $C_7$ & $C_8$ | 0.11 | 0.20 | 0.20 | 0.0 | 0.0 | 0.11 | 48.8 |
| Total, wt % | 100 | 100 | 100 | 100 | 100 | 100 | 100 |
| Flow, Kg/h | 14,956 | 15,966 | 15,966 | 1119 | 937 | 42 | 31 |

The comparison of the overall material balance of a continuous process with the process of Example 2 indicated that the major streams scale down linearly for the campaign case. Since the depropylenizer tower was eliminated, the C2/C3 to cracker in the campaign process was equivalent to the C2/C3 to cracker and depropylenizer side-draw purge streams combined from the continuous case. This stream was slightly higher, requiring about 2% more raffinate II feed.

The energy balance for the campaign case study, producing 5 KTA of polymer grade 1-hexene is given below. The energy balance for butene isomerization section, autometathesis section and hexane isomerization sections are given.

TABLE 23

Energy balance summary for improved batch process

| | $C_4$ Isom (2000 hours) | Autometathesis (2000 hours) | $C_6$ Isom (5333 hours) | Total |
|---|---|---|---|---|
| Feed vaporizer (LPS), KW | 1703 | 2364 | 1555 | |
| Feed Heater (fuel), KW | 114 | 344 | 297 | |
| Main Tower Condenser duty (CW), KW | 13,950 | | 9748 | |
| Main Tower Re-boiler duty (LPS), KW | 11,480 | | 7811 | |

TABLE 23-continued

Energy balance summary for improved batch process

| | $C_4$ Isom (2000 hours) | Autometathesis (2000 hours) | $C_6$ Isom (5333 hours) | Total |
|---|---|---|---|---|
| Depentenizer Condenser duty (CW), KW | | 2057 | 5149 | |
| Depentenizer Re-boiler duty (LPS), KW | | 1474 | 5147 | |
| Depentenizer distillate cooler (CW) | | 1743 | | |
| Pump, power, KW | 98 | 50 | 90 | |
| Total Utility | | | | |
| FUEL, KW | 114 | 344 | 297 | |
| CW, KW | 13950 | 3800 | 14897 | |
| LPS, KW | 13183 | 2364 | 14513 | |
| HPS, KW | | 1474 | | |
| POWER, KW | 98 | 50 | 90 | |
| Total Utility (8000 Hour Basis) | | | | |
| FUEL, KW | | | | 313 |
| CW, KW | | | | 14,369 |
| LPS, KW | | | | 13,562 |
| HPS, KW | | | | 379 |
| POWER, KW | | | | 97 |
| FUEL, MKCAL/H | | | | 0.217 |
| CW, MKCAL/H | | | | 12.32 |
| LPS, MKCAL/H | | | | 11.62 |
| HPS, MKCAL/H | | | | 0.32 |
| POWER, MKCAL/H | | | | 0.083 |

The energy consumption in the campaign process of Example 2 is increased by the elimination of certain energy integration. In the improved campaign operation of this example, the energy efficient two-tower $C_6$ separation system of Example 1 was replaced by a single tower separation to reduce the capital cost. Comparison of results in Tables 12 and 23 shows that the cooling water and low pressure steam usage nearly doubled in the Example 2 case. This is due to the elimination of two-tower separation system. The −5 deg C. refrigeration is eliminated in the improved batch process with a positive impact on operating cost. Example 2 shows that the capital cost savings realized by these improvements in the batch process as compared to Example 1 more than offset the increased utility cost for the small-scale plant.

The utility summary before exchange for the 50 KTA continuous case with high selectivity catalyst is given above in Table 13. The 5 KTA improved batch utility consumption is very similar to this result on a liner-prorated basis. The fuel usage decreased slightly as −5 deg C. as refrigeration is eliminated. The cooling water and LPS usage is higher. The capital cost savings realized by the equipment reduction in Example 2 as compared to Example 1 more than offset the increased utility cost for the 5 KTA plant.

Example 3

Campaign Process Employing Heat Pump

Simulations were conducted in the steady-state process simulator HYSYS using the PRSV property package. The analysis was carried out for a heat pump on the $C_4$/$C_6$ fractionator only, with conventional utilities used on the depentanizer/$C_6$ fractionator.

In this example, the process that was used corresponded to that shown in FIG. 3 along with the heat pump shown in FIG. 4. The $C_4$ overhead from fractionator 214 on FIG. 4 (corresponding to 114 on FIG. 3) contained 90 mol % butene-1. The fractionator in the isomerization section contained 100 theoretical stages and was operated at a reflux ratio of 29.9. The overhead pressure was 570 kPa, and the temperature profile for the fractionator operating in $C_4$ service is shown in FIG. 5. The ratio of recycle to fresh feed in the fractionator in the isomerization section was 2.4 to 1. The isomerization reactor was operated at 343 Deg. C. and 2948 kPa with 21% conversion of butene-2 to butene-1. Autometathesis took place at 315 Deg. C. and 1950 kpA. About 30% conversion of hexene-3 was obtained. The depentenizer was operated at 1200 kPa with 30 theoretical stages and a reflux ration of 1.0. The temperature profile of the depentenizer is shown in FIG. 6. The bottoms stream from the depentenizer contained 98 mol % hexene-3. In the isomerization reactor about 8.9% conversion to hexene-1 occurred. It is noted that condenser 224 on FIG. 4 is condenser 117 on FIG. 3 and reboiler 206 on FIG. 4 is reboiler 123 on FIG. 3.

Figure 7:
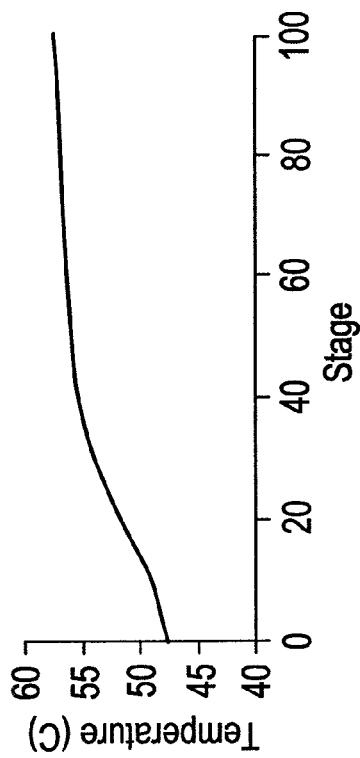
FIG. 7 is a graph showing the temperature profile of a first $C_6$ fractionator according to the embodiment of Example 3.
Figure 8:
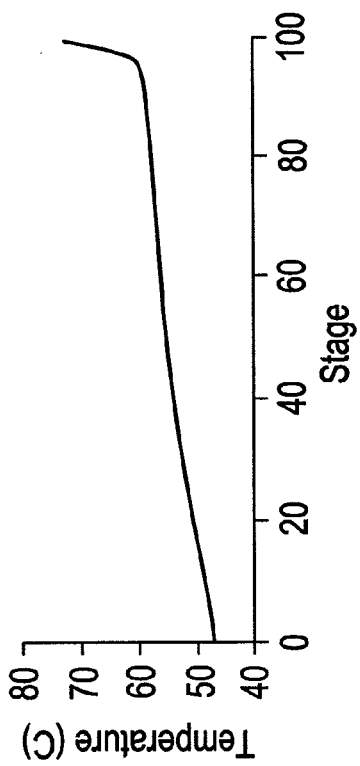
FIG. 8 is a graph showing the temperature profile of a second $C_6$ fractionator according to the embodiment of Example 3.

Using the 100 stage fractionator for $C_6$ processing, the fractionation reflux ratio for $C_6$ was 85.4 and the overhead pressure was 60 kPa. The overhead stream was separated to 92 mol % hexene-1. This stream was sent to the fractionator that previously had been run as a depentanizer. The overhead product obtained from the second fractionator, now in $C_6$ service, was 8.5 mol % hexene-1. The fractionator operated at a reflux ratio of 28.1 and an overhead pressure of 50 kPa. The bottoms stream was recycled to the isomerization reactor. Temperature profiles for the first and second fractionators when operated in C6 service are shown in FIGS. 6 and 7, respectively.

It was assumed that the compressor and expander were operated at constant discharge pressures for both $C_4$ and $C_6$ services. To achieve this, the pressure of the $C_6$ fractionator was adjusted downwardly to bring its temperature profile within the range of that of the $C_4$ fractionator. At the selected pressures of 570 kPa and 60 kPa for $C_4$ and $C_6$, respectively, the condenser and reboiler temperatures are given in Table 24.

TABLE 24

Condenser and Reboiler Temperatures

| Equipment | $C_4$ Fractionator 570 kPa | $C_6$ Fractionator 60 kPa |
|---|---|---|
| Condenser Temperature (C.) | 47.76 | 46.77 |
| Reboiler Temperature (C.) | 57.91 | 72.12 |

The limiting temperatures in Table 24 are the highest reboiler temperature and lowest condenser temperature. Therefore, the $C_6$ fractionator determined both the compressor and expander discharge pressures. Using 3° C. outlet temperature approaches with the outlet temperature approach being defined as the difference between the process fluid outlet temperature and the heat pump fluid outlet temperature, the compressor was required to raise the fluid boiling point to a minimum of 75.12 C, and the expander was required to lower the boiling point to a minimum of 43.77 C. For n-butane as a heat pump fluid, the required pressures for these boiling point temperatures, shown in Table 25, were 916.3 kPa and 420.9 kPa, respectively. Because the $C_6$ fractionator is limiting on both ends, the condenser and reboiler in $C_4$ service have temperature approaches greater than 3° C., with the most notable approach being 17.21° C. in the reboiler.

TABLE 25

Compressor and Expander Discharge

|  | Compressor | Expander |
|---|---|---|
| Temperature (C.) | 75.12 | 43.77 |
| Pressure (kPa) | 916.3 | 420.9 |

With the compressor and expander pressures fixed, the outlet temperature of heat exchanger 218 was set to the lowest achievable by cooling water, 38° C. With the boiling temperature fixed, subcooling to 38° C. provided additional cooling capacity, thus minimizing the fluid circulation rate through the heat pump. The circulation rate was then determined by the larger heat duty, which was the condenser. Setting the condenser outlet vapor fraction to one allowed the program to calculate the circulation rate, and setting the reboiler outlet vapor fraction to zero calculated the heat removed, which was the absolute heat duty difference between the reboiler and condenser, by heat exchanger 213.

The $C_4$ fractionator condenser and reboiler duties were greater than those of the $C_6$ fractionator. Constant compressor and expander discharge pressures (and thus boiling points) were maintained with varying fractionator duties by adjusting the heat pump circulation rate depending on the service. Thus, the minimum circulation rate to fully condense and vaporize the fluid throughout the cycle was employed. The heat pump circulation rate was 2,393 kgmol/h for the $C_4$ fractionator and 1,615 kgmol/h for the $C_6$ fractionator. Table 26 shows the circulation rates and heat duties for both towers.

TABLE 26

Heat Pump Data

|  | $C_4$ Fractionator | $C_6$ Fractionator |
|---|---|---|
| Circulation Rate (kgmol/h) | 2,393 | 1,615 |
| Condenser Duty (MW) | 13.95 | 9.75 |
| Reboiler Duty (MW) | 11.48 | 7.81 |
| E-1 Duty (MW) | 0.12 | 0.54 |
| E-2 Duty (MW) | 3.81 | 2.57 |

Analogous to the fractionator sizing for batch operation it is desirable to have $C_4$ and $C_6$ service require equal heat exchanger surface area in both the condenser and reboiler. The difference in heat duties is convenient, as the larger heat duties of the $C_4$ fractionator are also associated with larger LMTD due to the temperature constraints imposed by the $C_6$ operation. The required heat exchanger surface area can be approximated by calculating UA, given the heat duties and temperature approaches, for each exchanger. The calculation results are shown in Table 27.

$$UA = \frac{Q}{LMTD}$$

TABLE 27

Heat Exchanger Sizing

|  | Condenser | | Reboiler | |
|---|---|---|---|---|
|  | C4 Fractionator | C6 Fractionator | Depentanizer | C6 Fractionator |
| Heat Duty (MW) | 13.95 | 9.75 | 11.48 | 7.81 |
| LMTD (C) | 6.5 | 5.4 | 17.2 | 5.8 |
| UA (MW/C) | 2.14 | 1.74 | 0.67 | 1.26 |

It is noted that while neither the condensers nor the reboilers are an exact match, the difference in UA between $C_4$ and $C_6$ operation was compensated for by using different numbers of heat exchanger shells in series. For the cooling water exchangers in the heat pump loop, heat exchangers 213 and 218, the difference in duties was balanced by varying the cooling water flow rates.

In this example the minimum heat pump energy consumption was achieved in the following ways:

With the constraint that the compressor and expander operate at constant discharge pressures during $C_4$ and $C_6$ service, the minimum compressor work was obtained by choosing the lowest possible compressor discharge pressure and highest possible expander discharge pressure. In this way, the least amount of compressor work is done by the expander. To set these limits, the boiling temperatures of n-butane were chosen to be within the minimum temperature approach (3° C.) of the condenser and reboiler.

Cooling water was used in heat exchanger 218 to subcool to 38° C. before this stream entered the condenser. This maximized the low-cost additional cooling capacity, thus reducing the required circulation rate.

The minimum circulation rate was ensured by utilizing only the latent heat of the n-butane in both portions of the heat pump cycle. Heating or cooling into the region of sensible heat is less efficient on a per mass basis, thus requiring a higher circulation rate. In addition, only enough heat duty was removed in heat exchanger 213 (tantamount to undoing compressor work) to compensate for the difference in condenser and reboiler duties. The circulation rate can be lowered in $C_6$ service to adjust for the lower exchanger duties.

Example 4

Energy Consumption Analysis with and without Heat Pump

In this example, energy consumption was simulated for the cases that used and did not use a heat pump. When no heat pump is used, both the $C_4/C_6$ fractionator and depentanizer/$C_6$ fractionator have temperature profiles that permit the use of cooling water and steam in the condenser and reboiler, respectively. In the heat pump case it was assumed that electrical energy was required to drive the heat pump compressor. Alternately, high pressure steam can be used. The choice of compressor utility is dependent on many factors, such as cost, plant location, and availability, and thus should be considered on a case-by-case basis. The tower condenser and reboiler required no additional energy input. Cooling water can be used in the exchangers 113 and 118. Because the heat pump was applied only to the $C_4/C_6$ fractionator, the utilities of the depentanizer/$C_6$ fractionator number 2 were unchanged from the conventional case.

The analysis is summarized in Table 28. Energy costs were calculated and compared for one year of batch operation with the process operating in $C_4$ service for 2,000 hours and in $C_6$ service for 5,333 hours.

TABLE 28

Utility Summary

| Conventional Case (Duties in MW) | | C$_4$ Service (2000 h) | C$_6$ Service (5333 h) |
|---|---|---|---|
| Equipment | Utility Type | C$_4$ Fractionator | C$_6$ Fractionator |
| Condenser | Cooling Water | 13.95 | 9.75 |
| Reboiler | Steam | 11.48 | 7.81 |
| Equipment | Utility Type | Depentanizer | C$_6$ Fractionator #2 |
| Condenser | Cooling Water | 2.03 | 2.65 |
| Reboiler | Steam | 1.47 | 2.64 |
| Heat Pump Case (Duties in MW) | | C$_4$ Service (2000 h) | C$_6$ Service (5333 h) |
| Equipment | Utility Type | C$_4$ Fractionator | C$_6$ Fractionator |
| Compressor | Electrical | 1.60 | 1.08 |
| Heat Exc. 113 | Cooling Water | 0.12 | 0.54 |
| Heat Exc. 118 | Cooling Water | 3.81 | 2.57 |
| Equipment | Utility Type | Depentanizer | Second C6 Fractionator |
| Condenser | Cooling Water | 2.03 | 2.65 |
| Reboiler | Steam | 1.47 | 2.64 |

From Table 28, the condensers of the C$_4$ fractionator and depentanizer used 13.95 and 2.03 MW of cooling water duty, while the two C$_6$ fractionators used 9.42 and 2.65 MW, respectively. Cooling tower duty is valued at $0.50/MBtu. For one year of operation:

$$C4Cost = (13.95 + 2.03) \text{MW} \cdot \frac{1 \text{ Btu}}{1055 \text{ J}} \cdot \frac{\$0.50}{\text{MBtu}} \cdot 2000 \text{ h} \cdot \frac{3600 \text{ s}}{\text{h}} = \$54,500$$

$$C6Cost = (9.75 + 2.65) \text{MW} \cdot \frac{1 \text{ Btu}}{1055 \text{ J}} \cdot \frac{\$0.50}{\text{MBtu}} \cdot 5333 \text{ h} \cdot \frac{3600 \text{ s}}{\text{h}} = \$109,800$$

The reboilers of all but the depentanizer operated at low enough temperature to use low pressure (50 psig) steam, valued at $2.80/metric ton. From saturated steam tables, 50 psig steam has a latent heat of vaporization of 2121.6 kJ/kg.

$$C4Frac.Cost =$$
$$11.48 \text{ MW} \cdot \frac{1000 \text{ kW}}{\text{MW}} \cdot \frac{\$2.80}{1000 \text{ kg}} \cdot \frac{1 \text{ kg}}{2121.6 \text{ kJ}} \cdot 2000 \text{ h} \cdot \frac{3600 \text{ s}}{\text{h}} = \$109,100$$

-continued $$C6Frac.Cost = (7.81 + 2.64) \text{ MW} \cdot \frac{1000 \text{ kW}}{\text{MW}} \cdot \frac{\$2.80}{1000 \text{ kg}} \cdot \frac{1 \text{ kg}}{2121.6 \text{ kJ}} \cdot 5333$$
$$h \cdot \frac{3600 \text{ s}}{\text{h}} = \$251,600$$

The depentanizer reboiler operated at 178.8° C., thus requiring medium pressure (150 psig) steam, which has a saturation temperature of 185.6° C. Medium pressure steam was valued at $4.70/metric ton[4] and has a latent heat of vaporization of 1994.9 kJ/kg.

$$DeC5Cost =$$
$$1.47 \text{ MW} \cdot \frac{1000 \text{ kW}}{\text{MW}} \cdot \frac{\$4.70}{1000 \text{ kg}} \cdot \frac{1 \text{ kg}}{1994.9 \text{ kJ}} \cdot 2000 \text{ h} \cdot \frac{3600 \text{ s}}{\text{h}} = \$25,000$$

Total annual utility cost when no heat pump was included was $550,000. For a batch system without the heat pump producing 5 KTA of hexene-1 product, the utility cost is $0.110 per kilogram of hexene-1.

When a heat pump is included in the simulation, the heat pump compressor required 1.60 MW when operated on the C$_4$ fractionator, and 1.08 MW on the C$_6$ fractionator. The power values were calculated using an adiabatic efficiency of 75%. Electrical energy was valued at $0.02 per kW-h[4].

$$C4Cost = 1.60 \text{ MW} \cdot \frac{\$0.02}{\text{kWh}} \cdot \frac{1000 \text{ kW}}{\text{MW}} \cdot 2000 \text{ h} = \$64,100$$

$$C6Cost = 1.08 \text{ MW} \cdot \frac{\$0.02}{\text{kWh}} \cdot \frac{1000 \text{ kW}}{\text{MW}} \cdot 5333 \text{ h} = \$115,300$$

The cooling water required is that for E-1 and E-2. We take the same value as in the conventional case.

$$C4Cost = (0.12 + 3.81) \text{ MW} \cdot \frac{1 \text{ Btu}}{1055 \text{ J}} \cdot \frac{\$0.50}{\text{MBtu}} \cdot 2000 \text{ h} \cdot \frac{3600 \text{ s}}{\text{h}} = \$13,400$$

$$C6Cost = (0.54 + 2.57) \text{ MW} \cdot \frac{1 \text{ Btu}}{1055 \text{ J}} \cdot \frac{\$0.50}{\text{MBtu}} \cdot 5333 \text{ h} \cdot \frac{3600 \text{ s}}{\text{h}} = \$28,300$$

The utility cost for the depentanizer/C$_6$ fractionator, which remained the same as the conventional case, was $122,900. When included with the C$_4$/C$_6$ fractionator, the total utility cost for the heat pump case was $344,100 per year, or $0.069 per kilogram of hexene-1 product.

The cost calculations are summarized below in Table 29. It is noted that the heat pump case generated savings of 61% of the conventional energy consumption, and 37% of the energy cost. The savings are $0.041 per kilogram of hexene-1 product.

TABLE 29

Utility & Cost Summary

| | No Heat Pump | C4 Service (2000 h) | | C6 Service (5333 h) | |
|---|---|---|---|---|---|
| | | C4 Fractionator | | C6 Fractionator | |
| Equipment | Utility Type | Duty (MW) | Annual Cost | Duty (MW) | Annual Cost |
| Condenser | Cooling Water | 13.95 | $47,611 | 9.75 | $85,707 |
| Reboiler | Steam | 11.48 | $109,091 | 7.81 | $184,684 |
| | Total | 25.43 | $156,703 | 17.56 | $270,391 |

TABLE 29-continued

| | | Utility & Cost Summary | | | |
|---|---|---|---|---|---|
| | | Depentanizer | | C6 Fractionator #2 | |
| Equipment | Utility Type | Duty (MW) | Annual Cost | Duty (MW) | Annual Cost |
| Condenser | Cooling Water | 2.03 | $6,932 | 2.65 | $24,064 |
| Reboiler | Steam | 1.47 | $25,002 | 2.64 | $66,941 |
| | Total | 3.50 | $31,934 | 5.29 | $91,005 |
| Average Heat Duty (MW) | | 25.30 | | | |
| Total Cost | | $550,033 | ($0.110/kg hexene-1) | | |

| Heat Pump | | C4 Service (2000 hr) | | C6 Service (5333 h) | |
|---|---|---|---|---|---|
| | | C4 Fractionator | | C6 Fractionator | |
| Equipment | Utility Type | Duty (MW) | Annual Cost | Duty (MW) | Annual Cost |
| Compressor | Electrical | 1.60 | $64,067 | 1.08 | $115,311 |
| E-1 | Cooling Water | 0.12 | $417 | 0.54 | $4,939 |
| E-2 | Cooling Water | 3.81 | $13,005 | 2.57 | $23,399 |
| | Total | 5.53 | $77,488 | 4.19 | $143,650 |
| | | Depentanizer | | C6 Fractionator #2 | |
| Equipment | Utility Type | Duty (MW) | Annual Cost | Duty (MW) | Annual Cost |
| Condenser | Cooling Water | 2.03 | $6,932 | 2.65 | $24,064 |
| Reboiler | Steam | 1.47 | $25,002 | 2.64 | $66,941 |
| | Total | 3.50 | $31,934 | 5.29 | $91,005 |
| Average Heat Duty (MW) | | 9.69 | | | |
| Total Cost | | $344,077 | ($0.069/kg hexene-1) | | |
| Heat Duty Savings | | 61.7% | | | |
| Cost Savings | | 37.4% | ($0.041/kg hexene-1) | | |

For one year of campaign operation producing 5 KTA of hexene-1, the energy consumption and costs of the two cases, with and without the heat pump, are compared in Table 30. Inclusion of the heat pump saves 61% of the total duty and 37% of the utility cost of the conventional case.

TABLE 30

| | Utility Summary | | | |
|---|---|---|---|---|
| | Conventional Case | | Heat Pump Case | |
| Utility Type | Avg Duty (MW) | Annual Cost | Avg Duty (MW) | Annual Cost |
| Cooling Water | 13.1 | $164,314 | 5.8 | $72,756 |
| Steam | 10.8 | $385,719 | 2.3 | $91,943 |
| Compressor | 0.0 | $0 | 1.2 | $179,378 |
| Total | 23.9 | $550,033 | 9.4 | $344,077 |
| Savings | — | — | 60.8% | 37.4% |

In summary, the campaign process is different from the prior-known continuous process in the following ways:

1. The $C_4$ and $C_6$ fractionator/isomerization reactor systems are designed as a single unit. The system is operated for one period of time period of time as a $C_4$ isomerization/fractionation system and during another period of time as a $C_6$ isomerization/fractionation system.
2. With campaign processing, the combined fractionator/isomerization reactor system is shared. An intermediate storage tank is required to allow for this type of operation. In the batch system, the fractionator/isomerization reactor operates first in $C_4$ service to produce butene-1. This butene-1 can go to product butene-1, go further to autometathesis, or both. The autometathesis effluent produces lights for recovery, a recycle stream of $C_4/C_5$ olefins, and hexene-3 to fill a storage tank. The fractionator/isomerization reactor is then converted to $C_6$ service to produce hexene-1.
3. The third modification, in certain embodiments, is the inclusion of the closed loop heat pump with the working heat transfer fluid composition set to match both C4 and C6 operations. Using the same closed loop system for two different carbon number systems is unique. By operating in the campaign mode, the utility saving features of the cross exchange between the butene and hexene superfractionators is unavailable. This will result in higher utilities per unit hexene-1 product compared to the improved continuous process. To offset the added utility costs, a circulating heat transfer stream is alternately compressed and expanded to adjust its boiling point within the temperature range of the reboiler and condenser. The closed loop heat pump is used in these exchangers in place of conventional utilities. Flow rates and operating times are manipulated such that the design of the fractionator/isomerization reactor combination and the heat pump is amenable to both $C_4$ and $C_6$ service for use with the batch system.
4. In order to further reduce capital costs, the depentanizer is used as a topping column for hexene-1 purification. The fractionation duty required to produce high purity butene-1 is less than that required to produce hexene-1 (from their respective isomers). Thus a tower designed for both services has to be "oversized" for butene service to accommodate the hexene service. However, during the hexene-1 operation, the depentanizer tower is not in service in certain embodiments. Thus the fractionation capability of this tower can be used to provide the additional fractionation capacity for the hexene-1 purification thus allowing the main fractionator to be sized for butene service, resulting in additional capital savings.

The campaign processes described herein provide benefits over the conventional continuous process in three ways. First, the shared equipment of the campaign process reduces the total capital cost, as opposed to requiring dedicated equipment for $C_4$ and $C_6$ service. While the addition of the heat pump adds cost to the campaign process itself, its use results in a reduction in utility costs. Second, the campaign nature of the process and the flexibility to vary the operating times for each use of the isomerization technology allows for variation in production of butene-1 and/or hexene-1 depending upon changing market conditions. Third, the heat pump addresses the increase in energy consumption incurred by recycle of the isomerization effluent, affecting a comparable utility cost to that of a lower-yield process which forgoes the isomerization system.

It will be appreciated that various of the above-disclosed and other features and functions, or alternatives thereof, may be desirably combined into many other different systems or applications. Furthermore, it is noted that presently unforeseen or unanticipated alternatives, modifications, variations or improvements therein may be subsequently made by those skilled in the art which are also intended to be encompassed by the following claims.

What is claimed is:

1. A process for producing an alpha olefin comprising:
   obtaining a feed stream comprising an internal olefin having a first carbon number and an alpha olefin having a first carbon number,
   isomerizing the feed stream in a first isomerization reactor to increase the quantity of the alpha olefin having the first carbon number, forming a first isomerization effluent,
   fractionating the first isomerization effluent in a first fractionator to obtain a bottoms stream comprising the internal olefin having the first carbon number and an overhead stream comprising the alpha olefin having the first carbon number,
   subjecting the overhead stream to catalytic metathesis in a metathesis reactor under conditions and in the presence of a first metathesis catalyst to produce a mixed olefin effluent comprising an internal olefin having a second carbon number and other hydrocarbons,
   fractionating the mixed olefin effluent in a second fractionator to remove at least a portion of the other hydrocarbons and obtain an internal olefin intermediate,
   preparing the first isomerization reactor to receive the internal olefin intermediate,
   isomerizing the internal olefin intermediate in the prepared first isomerization reactor to form a second isomerization effluent comprising an increased quantity of alpha olefins having the second carbon number,
   preparing the first fractionator to receive the second isomerization effluent, and
   fractionating the second isomerization effluent in the prepared first fractionator to separate the alpha olefin having the second carbon number from the internal olefin having the second carbon number.

2. The process of claim 1, further comprising recycling at least a portion of the bottoms stream from the first fractionator to the first isomerization reactor.

3. The process of claim 1, wherein the olefins having a first carbon number are selected from the group consisting of $C_4$ to $C_6$ olefins.

4. The process of claim 1, wherein the olefins having a first carbon number are $C_4$ olefins and the olefins having a second carbon number are $C_6$ olefins.

5. The process of claim 1, further comprising using the second fractionator or a third fractionator to fractionate the second isomerization effluent.

6. The process of claim 1, wherein a portion of the alpha olefin having a first carbon number is withdrawn from the first fractionator as a product.

7. The process of claim 1, wherein the mixed olefin effluent comprises hydrocarbons having the first carbon number, and the process further comprises separating the hydrocarbons having the first carbon number from the mixed olefin effluent and recycling the separated hydrocarbons to the metathesis reactor.

8. The process of claim 1, wherein the first fractionator and/or the second fractionator employ a closed loop heat pump providing for heat exchange between an effluent condenser and a bottoms reboiler.

9. The process of claim 8, wherein preparing the first fractionator to receive the second isomerization effluent includes adjusting heat pump operating conditions.

10. The process of claim 8 where the closed loop heat pump uses as a working fluid a hydrocarbon or mixture of hydrocarbons such that the boiling point of that hydrocarbon or mixture falls between the boiling point of the alpha olefin having the first carbon number and the olefin having the second carbon number.

11. The process of claim 10 where the working fluid is n-butane when the first carbon number alpha olefin is butene-1 and the second carbon number alpha olefin is hexene-1.

12. The process of claim 8, wherein the heat pump further includes a vaporizer.

13. The process of claim 1, wherein the other hydrocarbons produced in metathesis include ethylene and/or propylene, and fractionating the mixed olefin effluent includes removing at least a portion of the ethylene and/or propylene as product.

14. The process of claim 1, wherein the other hydrocarbons produced in metathesis include ethylene, further comprising reacting the ethylene with butenes in the presence of a second metathesis catalyst to produce propylene.

15. The process of claim 1, wherein the mixed olefin effluent comprises pentene-2, further comprising reacting the pentene-2 with butene-1 to form propylene and hexene-3.

16. The process of claim 1, further comprising storing the internal olefin intermediate in a first storage tank during preparation of the first isomerization reactor and the first fractionator and then conveying the internal olefin intermediate from the first storage tank to the first isomerization reactor after preparation.

17. The process of claim 16, further comprising storing the bottoms stream comprising the internal olefin having the first carbon number in a second storage tank during preparation of the first isomerization reactor and the first fractionator and then conveying the internal olefin intermediate from the first storage tank to the metathesis reactor after preparation.

18. A process for producing hexene-1 comprising:
   obtaining a $C_4$ feed containing butene-1 and butene-2,
   isomerizing butene-2 to butene-1 in a first isomerization reactor, forming a first isomerization reactor effluent,
   fractionating the first isomerization reactor effluent in a first fractionator to form an overhead stream comprising butene-1 and a bottoms stream comprising butene-2, subjecting at least a portion of the overhead product to catalytic metathesis in a first metathesis reactor under conditions and in the presence of a first metathesis catalyst to produce a mixed olefin effluent comprising ethylene and hexene-3, fractionating the mixed olefin effluent in a second fractionator to form a hexene stream comprising hexene-3 and an overhead product stream comprising ethylene, preparing the first isomerization reactor to receive the hexene stream, isomerizing the hexene stream to foil a second isomerization effluent comprising hexene-1 and hexene-2 and the remaining hexene-3, preparing the first fractionator o receive the second isomerization effluent, and fractionating the second isomerization effluent in the prepared fractionator to obtain a hexene-1 stream.

19. The process of claim 18, wherein the $C_4$ feed is obtained from a reaction involving methanol or an ethylene oligomerization process.

20. The process of claim 18, further comprising removing at least a portion of the butene-1 from the overhead stream of the first fractionator as a butene-1 product.

21. The process of claim 18, further comprising reacting the butene-1 product with pentene-2 in the presence of a second metathesis catalyst to produce propylene and hexene-3.

22. The process of claim 18, further comprising reacting at least a portion of the butene-2 in the bottoms stream of the first fractionator with ethylene in the presence of a second metathesis catalyst to produce propylene.

23. The process of claim 18, further comprising recycling at least a portion of the bottoms stream to the first isomerization reactor.

* * * * *